(12) United States Patent
Cho

(10) Patent No.: US 9,707,332 B2
(45) Date of Patent: Jul. 18, 2017

(54) BLOOD PURIFYING APPARATUS

(71) Applicant: Taebeom Cho, Daejeon (KR)

(72) Inventor: Taebeom Cho, Daejeon (KR)

(73) Assignee: HUMAN BIOMED, INC

( * ) Notice: Subject to any disclaimer, the term of this patent is extended or adjusted under 35 U.S.C. 154(b) by 0 days.

(21) Appl. No.: 15/301,398

(22) PCT Filed: Mar. 31, 2015

(86) PCT No.: PCT/KR2015/003139
§ 371 (c)(1),
(2) Date: Oct. 2, 2016

(87) PCT Pub. No.: WO2015/152593
PCT Pub. Date: Oct. 8, 2015

(65) Prior Publication Data
US 2017/0095603 A1 Apr. 6, 2017

Related U.S. Application Data

(63) Continuation-in-part of application No. 14/243,137, filed on Apr. 2, 2014, now Pat. No. 9,585,994.

(30) Foreign Application Priority Data

Aug. 25, 2014 (KR) ........................ 10-2014-0110391
Feb. 3, 2015 (KR) ........................ 10-2015-0016434

(51) Int. Cl.
*A61M 1/34* (2006.01)
*A61M 1/36* (2006.01)
(Continued)

(52) U.S. Cl.
CPC ............ *A61M 1/3417* (2014.02); *A61M 1/16* (2013.01); *A61M 1/1623* (2014.02);
(Continued)

(58) Field of Classification Search
CPC ...... A61M 1/16; A61M 1/1623; A61M 1/267; A61M 1/3413; A61M 1/3417;
(Continued)

(56) References Cited

U.S. PATENT DOCUMENTS

2010/0282662 A1 11/2010 Lee et al.

FOREIGN PATENT DOCUMENTS

JP 2011-019685 A 2/2011
KR 10-2006-0057176 5/2006
(Continued)

OTHER PUBLICATIONS

International Search Report for—English (PCT/KR2015/003139 ) Mailed Jul. 24, 2015.
(Continued)

*Primary Examiner* — John Kim
(74) *Attorney, Agent, or Firm* — Lee Global Patent, LLC

(57) ABSTRACT

Provided is a multi-functional filter including a first filter and a second filter to purify a biological fluid, a housing defining an adsorption section outside of the first filter and the second filter, a flow partitioning connector connecting the first filter and the second filter, and a housing port allowing a fluid to flow through the adsorption section. The housing may comprise a wall, a first cap coupled to the first filter at one end of the wall along a longitudinal direction, and a second cap coupled to the second filter at the other end of the wall along a longitudinal direction. The multi-functional filter according to the present invention in which dialysis, adsorption, and plasma separation or ultrafiltration are integrated to purify blood or dialysate and the internal flow is facilitated may provide a blood purifying apparatus that simplifies the whole apparatus, provides convenience in installation and use, and reduces a treatment cost.

16 Claims, 21 Drawing Sheets

(51) Int. Cl.
*A61M 1/16* (2006.01)
*B01D 63/04* (2006.01)
*B01D 61/18* (2006.01)
*B01D 61/24* (2006.01)
*A61M 1/26* (2006.01)

(52) U.S. Cl.
CPC .......... *A61M 1/267* (2014.02); *A61M 1/3413* (2013.01); *A61M 1/3472* (2013.01); *A61M 1/3496* (2013.01); *A61M 1/3679* (2013.01); *B01D 61/18* (2013.01); *B01D 61/243* (2013.01); *B01D 63/04* (2013.01); *B01D 63/043* (2013.01); *A61M 2205/75* (2013.01); *B01D 2311/25* (2013.01); *B01D 2311/2626* (2013.01); *B01D 2313/21* (2013.01); *B01D 2313/40* (2013.01); *B01D 2313/54* (2013.01); *B01D 2319/02* (2013.01)

(58) Field of Classification Search
CPC .............. A61M 1/3472; A61M 1/3479; A61M 1/3486; A61M 1/3496; A61M 1/3679; A61M 2205/75; B01D 2311/25; B01D 2311/2626; B01D 2311/2649; B01D 2313/54; B01D 2313/21; B01D 2319/02; B01D 61/18; B01D 63/04; B01D 63/043; B01D 2313/40; B01D 61/243; B01J 20/2805

See application file for complete search history.

(56) References Cited

FOREIGN PATENT DOCUMENTS

| KR | 10-2009-0027173 | 3/2009 |
| KR | 10-2013-0086624 | 8/2013 |
| KR | 10-2014-0077804 | 6/2014 |

OTHER PUBLICATIONS

Written Opinion of the International Search Authority—Eng (PCT/KR2015/003139), (Oct. 4, 2016).

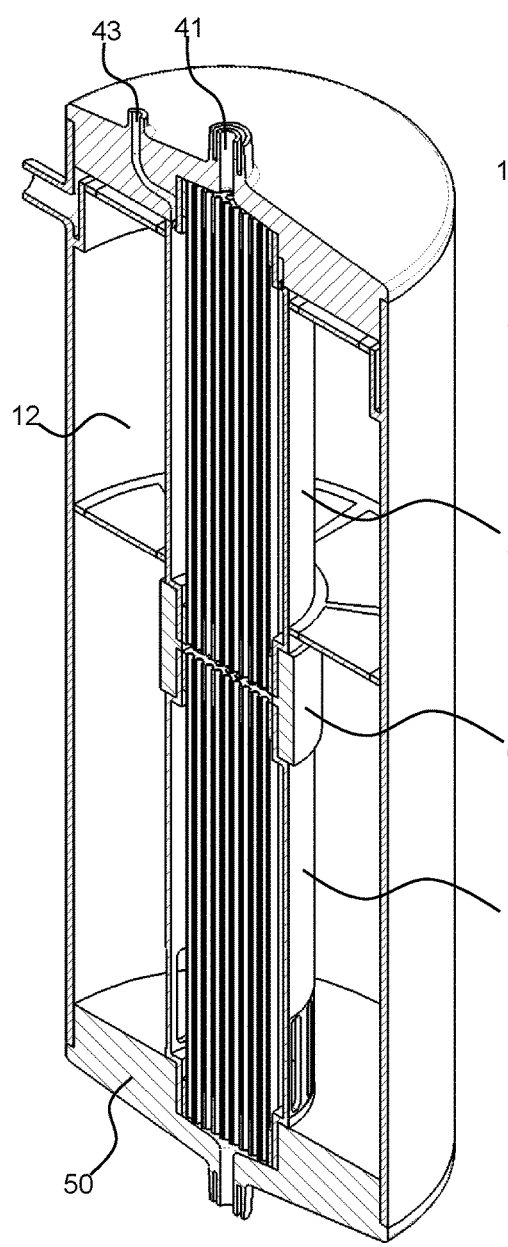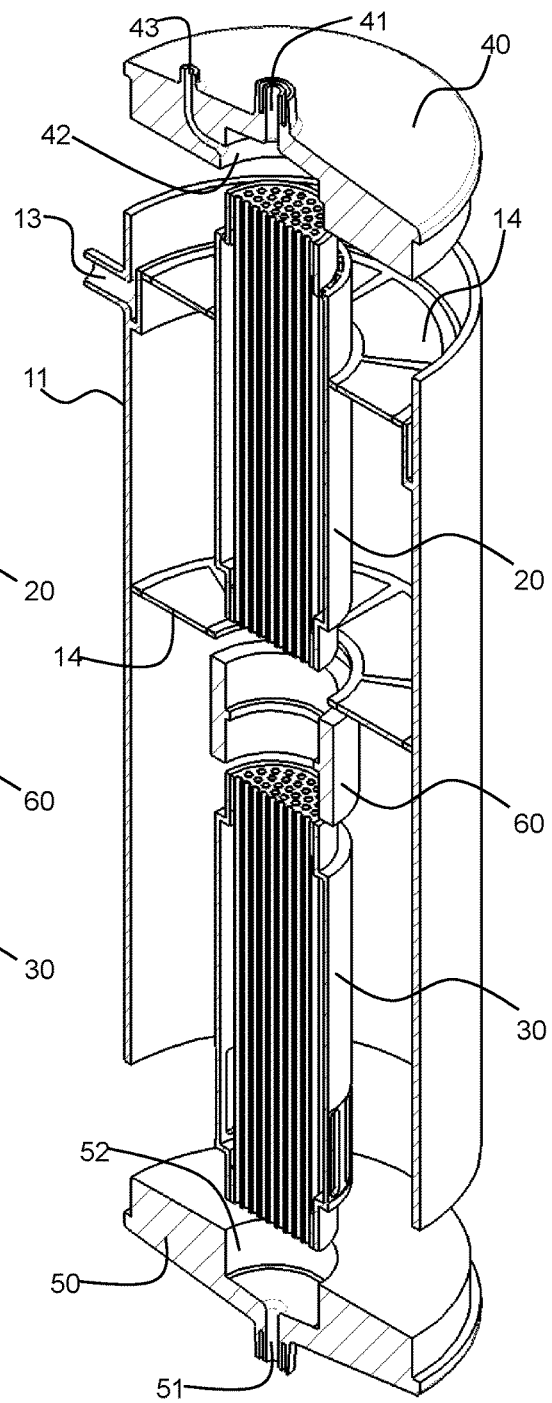
SECTION A-A
FIG. 2A
FIG. 2B

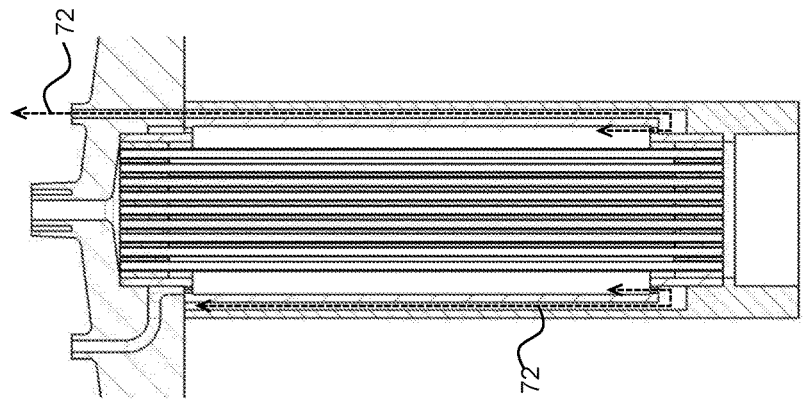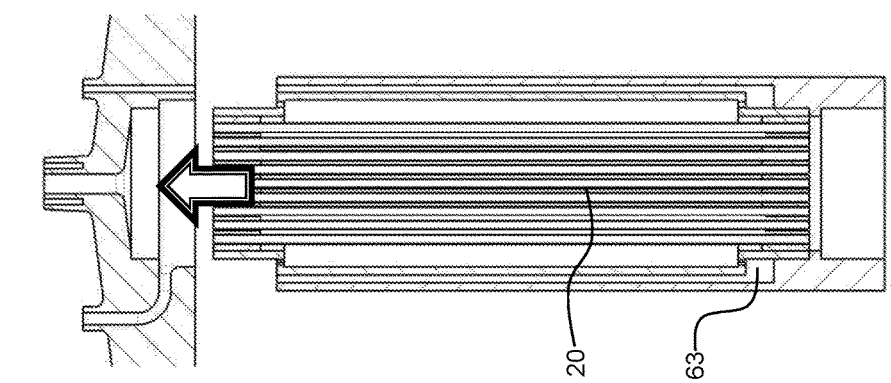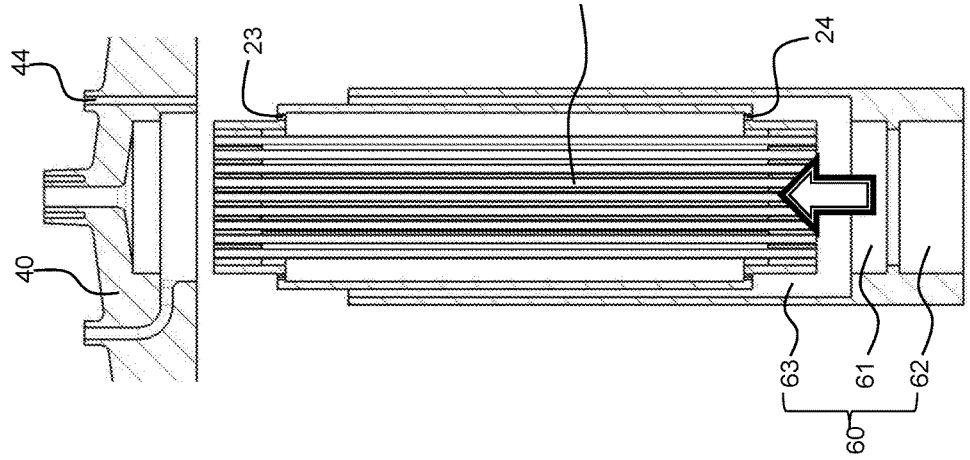

FIG. 16A   SECTION A-A

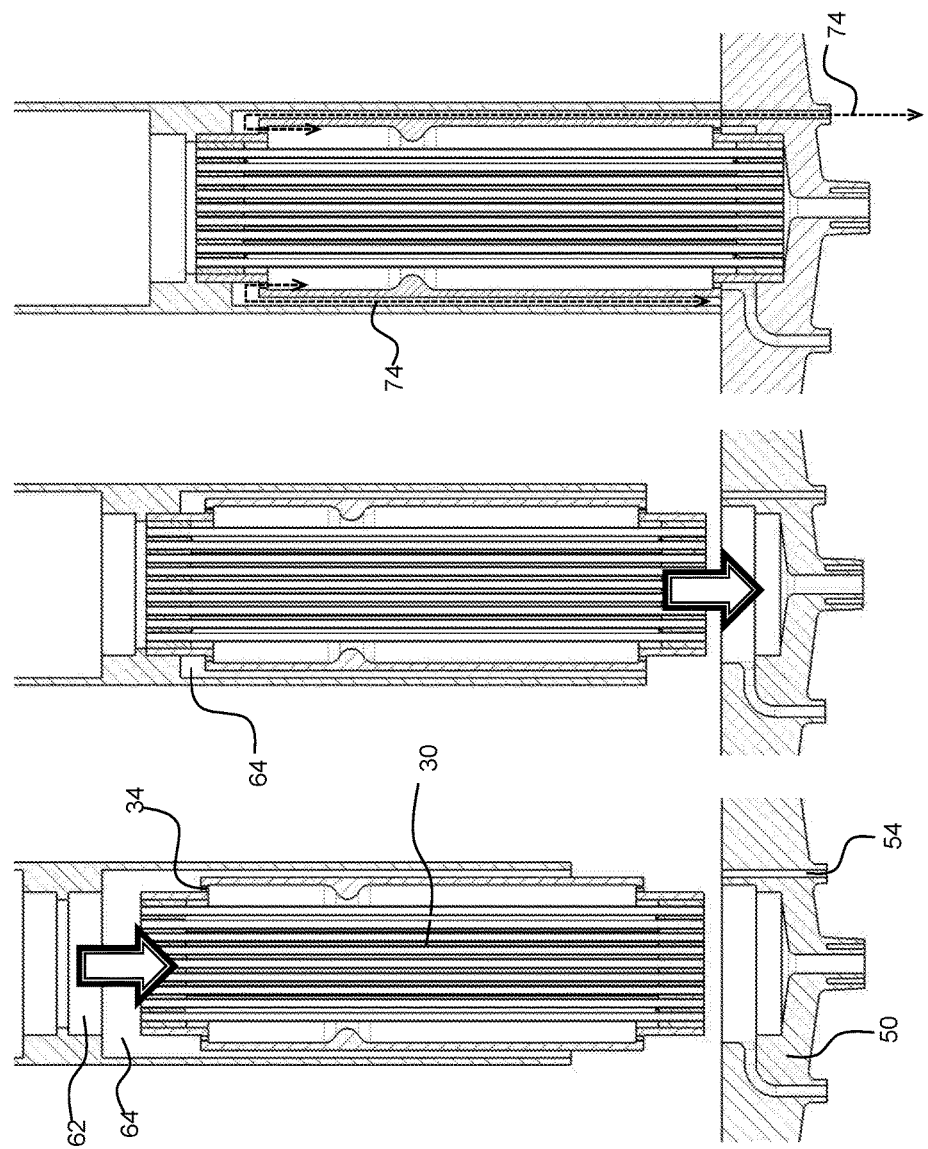

FIG. 20A SECTION A-A

BLOOD PURIFYING APPARATUS

TECHNICAL FIELD

The present invention relates to a blood purifying apparatus to rid blood of toxins and waste products, and more particularly, to a blood purifying apparatus which is simplified, provides convenience in installation and use, and reduces a treatment cost, using a multi-functional filter in which a function of dialysis, a function of adsorption, and a function of ultrafiltration or plasma separation are integrated.

BACKGROUND

Liver performs many essential functions, such as a metabolic function of treating various nutrients, a function to synthesize plasma protein, e.g., albumin, and a function of detoxifying toxins such as alcohol or drug. Also, a kidney performs functions of discharging urea nitrogen which is a metabolite of a protein, removing extra water inside a body, and regulating blood pressure. When a liver is damaged, the substances that have to be removed from a body by the hepatic metabolism, such as ammonia and bilirubin, are accumulated in the body. The accumulation causes complications such as jaundice, hepatic encephalopathy, acute kidney failure, systemic inflammation, and multiple organ failure. Similarly, when there is a kidney dysfunction, water and protein-metabolic substances which need to be removed out of the body are accumulated, causing complications such as uremia and cardiovascular disease.

In case of acute liver failure, although a liver transplant is regarded as the only cure, according to the liver transplant data published by OPTN/SRTR Annual Report in 2011, only 36% of the patients waiting for a liver transplant actually receive the treatment. Organ transplantation data from Korean Network for Organ Sharing (KONOS) also show that only 22% of the patients on the waiting list receive the liver transplant, because the number of donor liver is substantially short as compared with the number required for the liver transplant. Similarly, in the case of the kidney transplant, approximately 30% of patients with end-stage renal disease receive the kidney transplant. Thus, when the liver transplant or the kidney transplant is not performed in a timely manner, a treatment is required for purifying blood in which blood is circulated out of body and toxins are removed through various methods, such as dialysis, filtration, or adsorption.

Artificial liver apparatuses currently in clinical use are limited only to MARS of Gambro and Prometheus of FMC. Prometheus has such configuration that plasma is separated from blood to be filtered through ion-exchange resin adsorbent for removal of toxins existing in the plasma and then hemodialysis is performed after the plasma separation and adsorption. Accordingly, Prometheus apparatus ends up with a complicated system including a plasma separation filter, two adsorption filters removing toxins from plasma, and hemodialysis process, giving rise to a high treatment cost.

MARS is configured to remove hepatic toxins from blood using a dialyzer in which mass transfer occurs between blood and dialysate when blood and dialysate flow with a semi-permeable membrane therebetween as seen in a general hemodialysis apparatus. However, as MARS is compared with a general hemodialysis apparatus required for patients with renal failure, it is characterized by the use of a plasma protein called albumin which is added to the dialysate, such that hepatic toxins, various protein-bound toxins, as well as uremic toxins can be removed. Here, the albumin needs to be regenerated, which necessitates an additional hemodialyzer, activated charcoal and ion-exchange resin filters. Accordingly, due to the several stages of dialysis and adsorbent filters required for MARS treatment, as well as the expensive albumin, MARS comes to a complicated system and a costly treatment like Prometheus.

DISCLOSURE

Technical Problem

The present invention provides a blood purifying apparatus that simplifies the whole apparatus, provides convenience in installation and use, and reduces the treatment cost by using a multi-functional filter in which dialysis, adsorption, and ultrafiltration or plasma separation are integrated.

Technical Solution

Provided is a multi-functional filter including a first filter and a second filter to purify a biological fluid, a housing defining an adsorption section outside of the first filter and the second filter, and a housing port allowing a fluid to flow through the adsorption section. The housing may comprise a wall, a first cap coupled to the first filter at one end of the wall along a longitudinal direction, and a second cap coupled to the second filter at the other end of the wall along a longitudinal direction. Also, the multi-functional filter may further include a flow partitioning connector connecting the first filter and the second filter to prevent a leakage of a blood therebetween.

The first filter and the second filter may have a structure where a cylinder-shape container is charged with a semi-permeable membrane and port-processed at both ends thereof by use of a synthetic resin like polyurethane. The internal space of the first filter container and the second filter container can be divided into two flow regions to allow two fluids to flow therethrough.

Here, the first filter container and the second filter container may have a flow hole in at least one of two opposite sides separated along a longitudinal direction with respect to a longitudinal middle portion of the container. For example, a first hole may be provided in the first filter container at a side to which the first cap is connected, and a third hole may be provided in the second filter container at a place close to the second cap.

The first cap and the second cap may include a cap port to allow fluid to pass therethrough and a connecting portion coupled to the filter. When the cap is coupled to the filter, a fluid passing through the cap port is configured to flow through a side of the filter membrane. Also, at least one of the first cap and the second cap may include a flow passage penetrating the cap, an end of which is adjacent to the connecting portion of the cap. For example, the first cap may include a first flow passage, opposite ends of which are adjacent to the first cap connecting portion and an outer surface of the cap.

When the first cap is coupled to the first filter, the first flow passage forms a flow path through which fluid flows into the first filter. One side of the first filter container is seated in the connecting portion of the first cap, and the first filter and the first cap are coupled to each other. The coupling of the first filter and the first cap forms the first flow path in which the fluid passing through the first flow passage provided in the first cap can flow into the first filter through the first flow hole of the first filter container.

An adsorbent may be provided in the adsorption section to remove toxins and waste products. Exemplary adsorbents according to an embodiment of the present invention include an anion exchange resin and activated charcoal. An anion exchange resin removes electrically charged toxins, such as bilirubin, while being combined with plasma proteins by means of ion exchange mechanism. On the other hand, activated charcoal may be used to remove tryptophan and water-soluble middle-sized toxins by physical adsorption. The adsorbent included in the multi-functional filter is not limited in the type and number, and may be modified according to a patient requiring the blood purifying treatment.

The housing port and the third flow hole may be desirably provided in the opposite side of each other with respect to a longitudinal middle portion of the container, such that a fluid flowing into the adsorption section through the housing port can sufficiently contact the adsorbent and then move to the second filter. In this case, the adsorbent must not move through the housing port or the flow hole and various methods may be used to prevent the passing of adsorbents. For example, the housing port or the flow hole may be formed to have a size smaller than the adsorbent, or may be covered by a mesh filter with pores having a smaller size than the adsorbent. Alternatively, a separation wall may be disposed between the adsorbent and the housing port or between the adsorbent and the flow hole.

The multi-functional filter may or may not make direct contact with blood of a patient according to an exemplary embodiment of the blood purifying apparatus. When the multi-functional filter makes contact with blood, the blood purifying apparatus may include the multi-functional filter, a tube connecting the multi-functional filter and a patient, a pump disposed on the tube to transfer blood. Hemodialysis and plasma separation occur in the first filter and the second filter, respectively.

When blood flows into the multi-functional filter, plasma is separated from blood in the second filter. The separated plasma flows into the adsorption section through the third flow hole, and toxins and waste products are removed from the plasma due to the contact with adsorbent. The plasma passing the adsorption section returns, through the housing port, to the tube in which blood flows. Remaining blood of the second filter flows into the first filter through the flow partitioning connector and hemodialysis takes place therein. The dialysate may be supplied to the first filter and then discharged therefrom through the first flow path which connects the first flow hole and the first flow passage. Dialysate may be used in a form of a dialysate bag or manufactured by adjusting, e.g., pH and electrolyte concentration in the ultrapure water prepared through a water treatment system.

On the other hand, when the multi-functional filter does not make direct contact with blood of a patient, the blood purifying apparatus according to an embodiment of the present invention may include a blood filter in which mass transfer occurs between blood and dialysate, a tube connecting the blood filter and a patient, in which blood or dialysate flow, and a pump disposed on the tube to transfer blood or dialysate, and the multi-functional filter to purify the used dialysate. In this case, dialysis and ultrafiltration may take place in the first filter and the second filter, respectively. The multi-functional filter removes toxins and waste products from the used dialysate and adjusts electrolyte concentration, thereby regenerating the dialysate.

Advantageous Effect

The blood purifying apparatus according to an embodiment of the present invention not only efficiently purifies blood, but also simplifies the whole apparatus, provides convenience in installation and use, and reduces a treatment cost by using the multi-functional filter in which the hemodialysis through the first filter, the plasma separation or ultrafiltration through the second filter, and the adsorption in the adsorption section are integrated.

BRIEF DESCRIPTION OF DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIGS. 2A and 2B are a perspective view and an exploded view illustrating a multi-functional filter according to an embodiment of the present invention;

FIGS. 12A, 12B and 12C are cross-sectional views illustrating a coupling structure of a first cap, a first filter, and a flow partitioning connector;

FIGS. 16A and 16B are a cross-sectional view and a perspective view illustrating a multi-functional filter having a fourth flow passage;

FIGS. 18A, 18B and 18C are cross-sectional views illustrating a coupling structure of a second cap, a second filter and a flow partitioning connector;

FIGS. 20A and 20B are a cross-sectional view and a perspective view of a multi-functional filter having a flow partitioning connector hole, respectively;

BEST MODE

Figure 1:
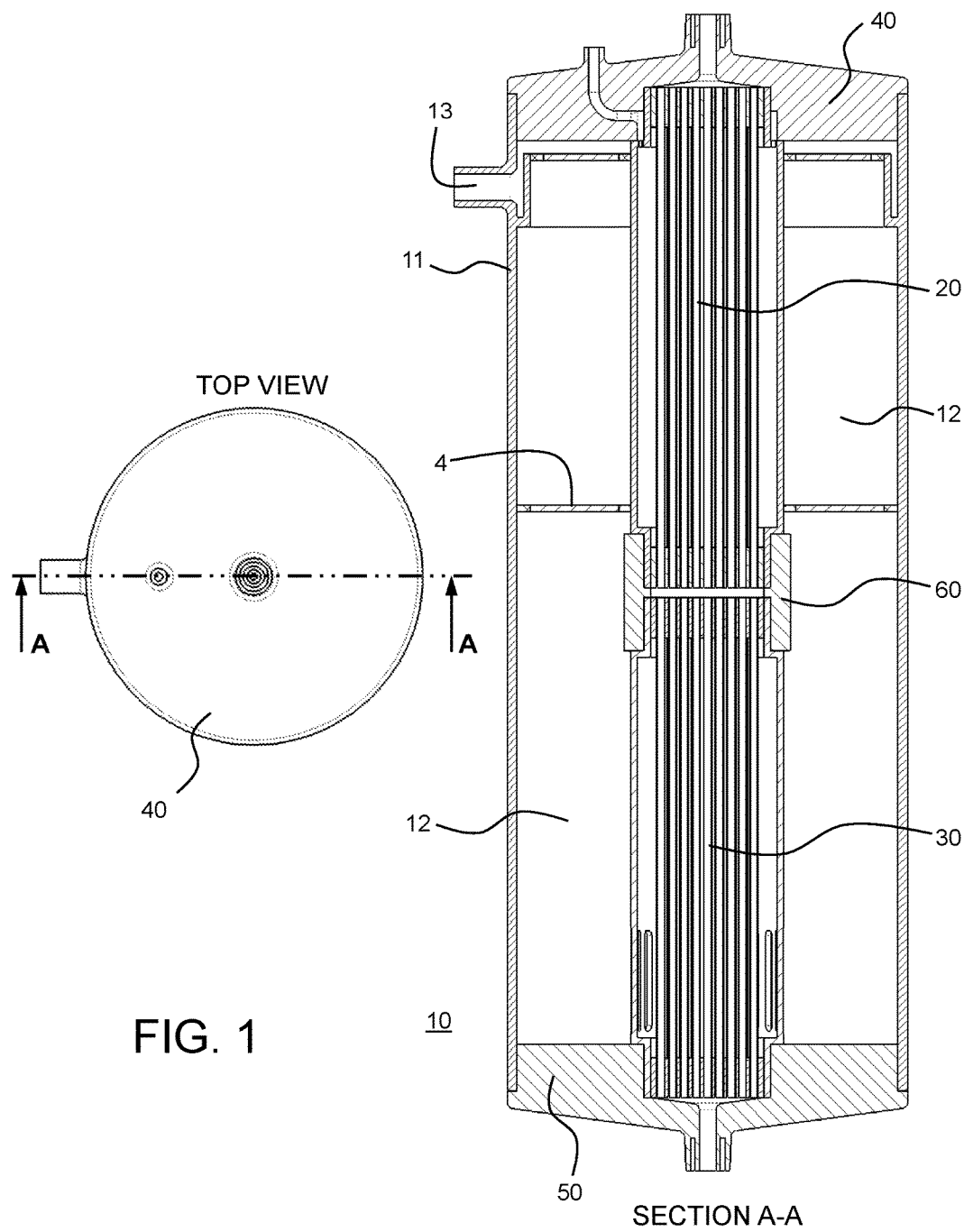
FIG. 1 is a cross-sectional view of a multi-functional filter according to an embodiment of the present invention.

Hereinafter, a multi-functional filter and a blood purifying apparatus having the multi-functional filter according to an embodiment of the present invention will be described in detail with reference to the accompanying drawings.

In the following description of the present invention, the size, shape or the like of constituent elements illustrated in the drawings may be exaggerated or simplified for clarity and convenience of explanation. Also, the terms particularly defined taking into consideration the configurations and operations of the present invention may be changed based on the intentions of users or operators, or customs. These terms should be construed as meanings and concepts conforming to the technical spirit of the present invention based on the general context of this specification.

Figures 3A, 3B, 3C:
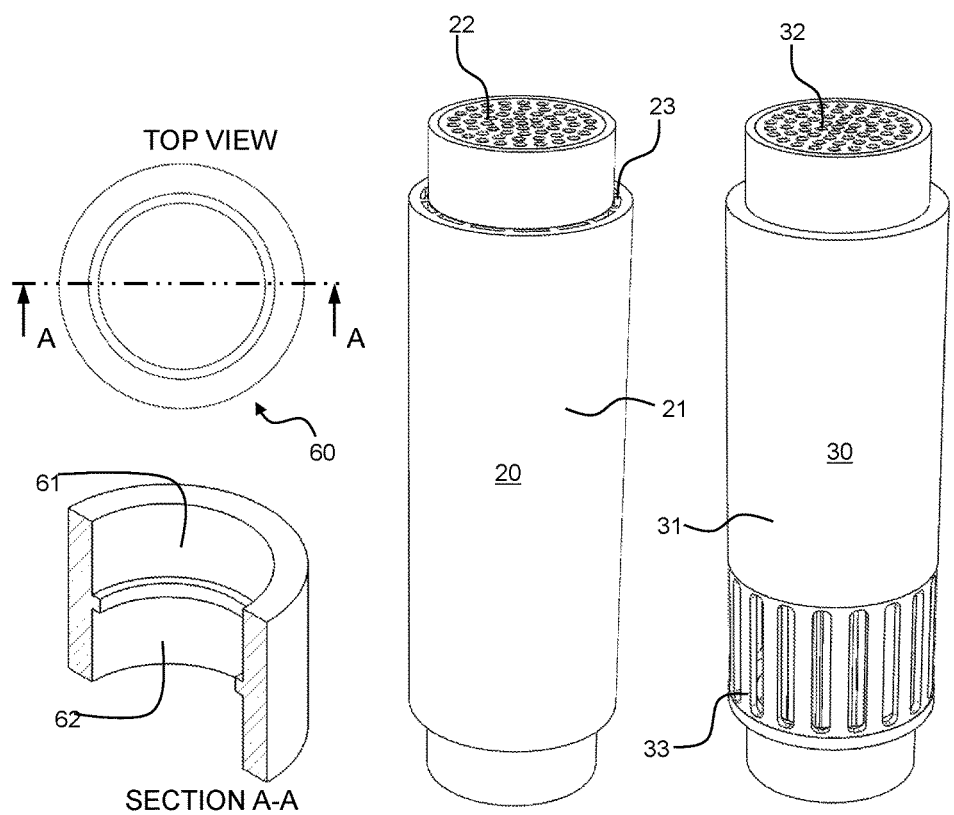
FIGS. 3A, 3B, and 3C are views illustrating a flow partitioning connector, a first filter and a second filter, respectively.

As shown in FIGS. 1, 2A and 2B, the multi-functional filter 10 according to an embodiment of the present invention includes a first filter 20, a second filter 30, a housing and a housing port 13. The first filter and the second filter purify a biological fluid, such as blood, plasma, or used dialysate. The housing provides installation spaces for the first filter and the second filter and defines an adsorption section 12 outside the first filter and the second filter. The housing port provided in the housing allows a fluid to flow through the adsorption section. The housing includes a wall 11, a first cap 40 coupled to the first filter 20 at a side of the wall along a longitudinal direction, and a second cap 50 coupled to the second filter at the other side of the wall along a longitudinal direction. The multi-functional filter 10 according to an embodiment of the present invention may further include a flow partitioning connector 60 that connects the first filter and the second filter to prevent a leakage of blood. As shown in FIG. 3A, the flow partitioning connector may have connecting portions 61 and 62 which are connected to the first filter and the second filter, respectively.

Referring to FIGS. 3B and 3C, the first filter 20 and the second filter 30 may have a structure where a cylinder-shape container 21 and 31 is charged with a semi-permeable membrane 22 and 23 and port-processed at both ends thereof by use of a synthetic resin like polyurethane. A hollow-fiber membrane type filter that includes a hollow-fiber type membrane is illustrated in the drawings. The hollow-fiber membrane type filter is advantageous in that it has excellent mass-transfer efficiency resulting from large effective surface area compared to the small size as a whole. However, the first filter and the second filter are not limited thereto, but may be modified to include other types of membrane, such as a flat membrane. The internal space of the first filter container 21 and the second filter container 31 can be divided into two flow regions to thus allow two fluids to flow therethrough.

Here, the first filter container 21 and the second filter container 31 may have a flow hole in at least one of two opposite sides separated along a longitudinal direction with respect to a longitudinal middle portion of the container. For example, as shown in FIGS. 3B and 3C, a first hole 23 may be provided in the first filter container 21 at a side to which the first cap is connected, and a third hole 33 may be provided in the second filter container 31 at a place close to the second cap. A plurality of flow holes 23 and 33 may be provided to surround the containers 21 and 31 along a circumferential direction.

As shown in FIG. 2, the first cap 40 may include a first cap port 41 to allow fluid to pass therethrough and a first cap connecting portion 42 coupled to the first filter, and when the first cap is coupled with the first filter, a fluid passing through the first cap port 41 is configured to flow through a side of the first filter membrane 22 or through the inside of the hollow-fiber membrane. Similarly, the second cap 50 may include a second cap port 51 and a second cap connecting portion 52 coupled to the second filter, and when the second cap is coupled to the second filter, a fluid passing through the second cap port is configured to flow through a side of second filter membrane 32. The first cap connecting portion 42 and the second cap connecting portion 52 depicted in the drawing have a shape of concave groove to which one side of the filter can be inserted. However, the connecting portions 42 and 52 are not limited to the shape shown in the drawing, but may be modified to have a different size and shape to thereby allow the filter and the cap to be coupled to each other.

Also, at least one of the first cap 40 and the second cap 50 may include a flow passage penetrating the cap, an end of which is adjacent to the connecting portion 42 or 52 of the cap. For example, as shown in FIG. 2, the first cap may include a first flow passage 43, opposite ends of which are adjacent to the first cap connecting portion 42 and an outer surface of the cap. The outer surface of the cap represents, e.g., a side surface of the cap or the surface where the cap port 41 or 51 is disposed, other than the surface facing the adsorption section 12.

Figure 4:
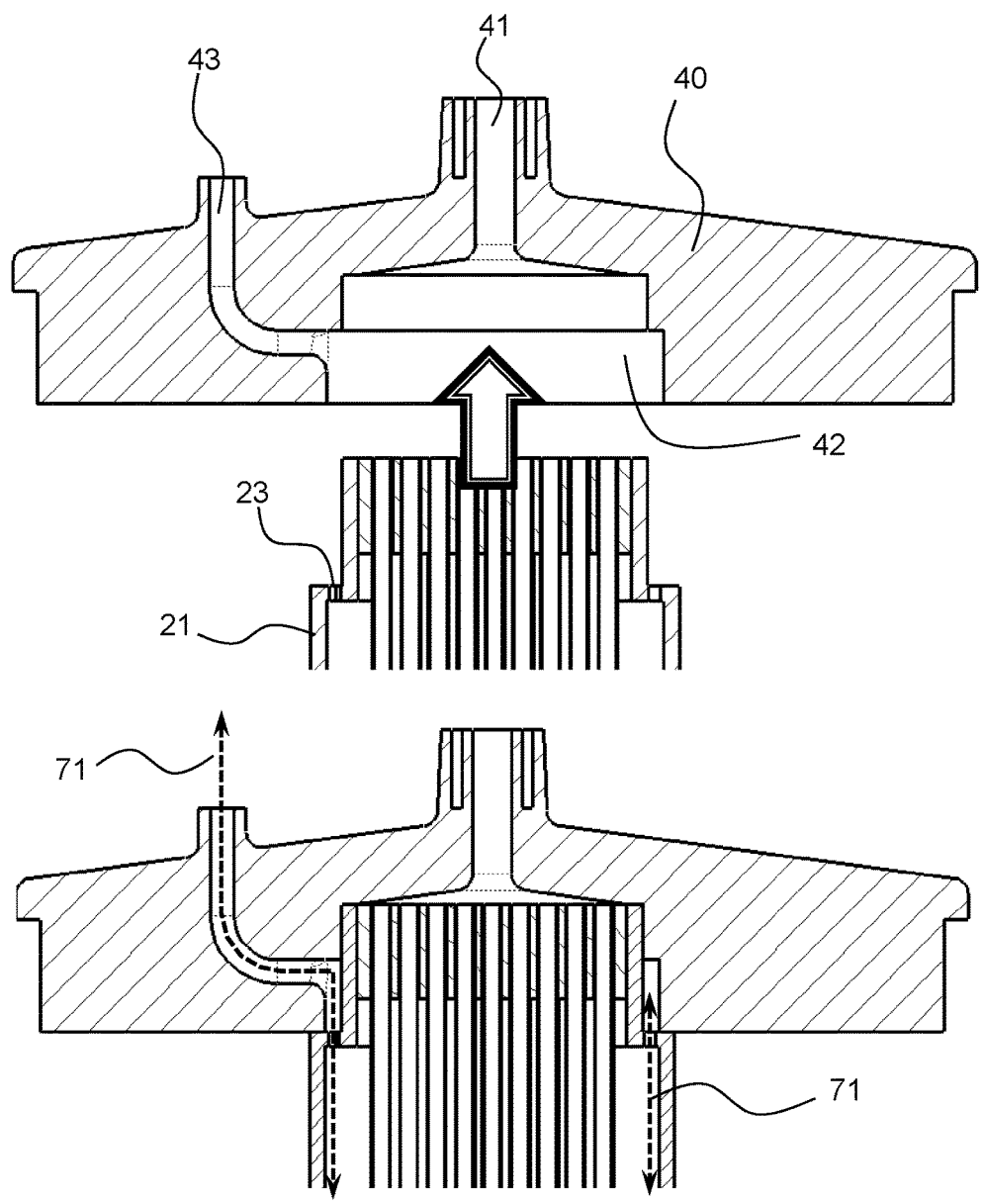
FIG. 4 is a cross-sectional view illustrating a coupling structure of a first cap and a first filter.

When the first cap is coupled to the first filter, the first flow passage 43 forms a flow path through which fluid flows into the first filter. FIG. 4 illustrates a first flow path 71 which is formed by the coupling of the first cap 40 and the first filter 20. One side of the first filter container 21 is seated in the connecting portion 42 of the first cap and the first filter and the first cap are coupled to each other. The coupling of the first filter and the first cap forms two flow paths. For example, the fluid passing through the first cap port 41 is configured to flow through one side of the first filter membrane 22, and the fluid passing through the first flow passage 43 provided in the first cap can flow into the first filter through the first flow hole 23 of the first filter container. Accordingly, the coupling of the first filter and the first cap forms the first flow path 71 that connects the first flow passage 43, the first flow hole 23, and the first filter 20.

As such, due to the coupling of the cap 40 or 50 and the filter 20 or 30, the fluid is limited to flow into a predetermined region. Various methods may be used, such as chemical adhesion of each coupling part of the cap and filter or insertion of a soft O-ring such as silicone into each adhesion part, to prevent fluids from flowing to other spaces except the predetermined spaces.

An adsorbent may be provided in the adsorption section 12 to remove toxins and waste products. Exemplary adsorbents according to an embodiment of the present invention include an anion exchange resin and activated charcoal. An anion exchange resin removes electrically charged toxins, such as bilirubin, while being combined with plasma proteins by means of ion exchange mechanism. On the other hand, activated charcoal may be used to remove tryptophan and water-soluble middle-sized toxins by physical adsorption. The adsorbent may be used in a form of powder, particle, or block in which powder and particles are compressed. The adsorbent included in the multi-functional filter according to an embodiment of the present invention is not limited in the type and number, and may be modified according to a patient requiring the blood purifying treatment.

The housing port may be desirably provided in the first cap 40 or on the wall 11 at a side close to the first cap, and the third flow hole may be provided in the second filter container at a side close to the second cap, such that a fluid flowing into the adsorption section 12 through the housing port 13 can sufficiently contact the adsorbent inside the adsorption section 12 and then move to the second filter through the third flow hole 33 provided in the second filter container 31. In the case of flow in an opposite direction, the fluid in the second filter can flow into the adsorption section through the third flow hole and pass through the adsorption section, and then be discharged through the housing port.

Figure 5:
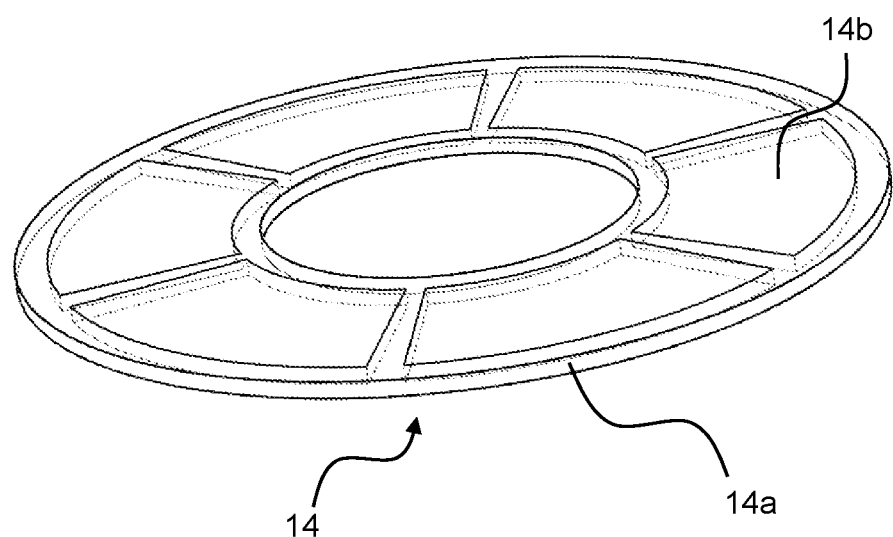
FIG. 5 is a perspective view of a separation wall.

In this case, the adsorbent must not move through the housing port 13, and the first flow hole 23 or the third flow hole 33, and various methods may be used to prevent the passing of adsorbents. For example, the housing port or the flow hole may be formed to have a size smaller than the adsorbent, or may be covered by a mesh filter with pores having a smaller size than the adsorbent. Also, the adsorbent may be covered by a mesh filter with pores having a smaller size than the adsorbent itself, or an adsorbent block in which powder or particles are compressed may be used. Alternatively, as shown in FIG. 2, a separation wall 14 may be disposed between the adsorbent and the housing port or between the adsorbent and the flow hole. The separation wall 14 may have pores of a smaller size than the adsorbent to inhibit the passing of adsorbent, or may be manufactured to have a structure in which a mesh filter 14b having pores of a smaller size than the adsorbent is attached to a support wall 14a through which a fluid can flow, as illustrated in FIG. 5.

Similarly, when two or more kinds of adsorbent are used, the adsorbents may be covered by a mesh filter with pores of a smaller size than the adsorbents in order to prevent the adsorbents from mixing. Also, an adsorbent block in which powder or particles are compressed may be used, or the separation wall 14 may be disposed between the adsorbents.

Hereinafter, the blood purifying apparatus 80 including the multi-functional filter 10 will be described in detail with reference to the accompanying drawings.

Figure 6A:
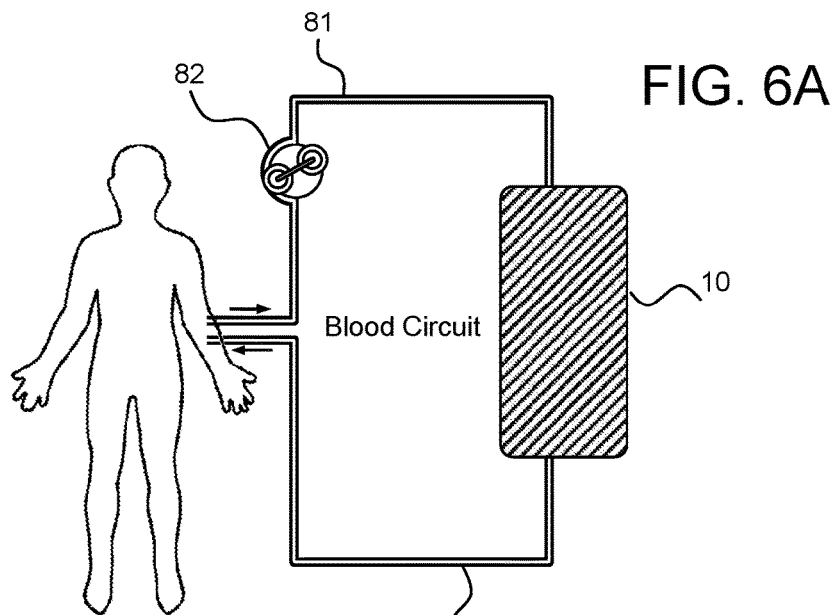
FIGS. 6A and 6B are schematic views of a blood purifying apparatus according to an embodiment of the present invention.

The multi-functional filter may or may not make direct contact with blood of a patient according to an exemplary embodiment of the blood purifying apparatus. When the multi-functional filter makes contact with blood, as shown in FIG. 6A, the blood purifying apparatus may include the multi-functional filter 10, a tube connecting the multi-functional filter and a patient, a pump 82 disposed on the tube to transfer blood. In this case, hemodialysis and plasma separation may occur in the first filter and the second filter, respectively.

Figure 7:
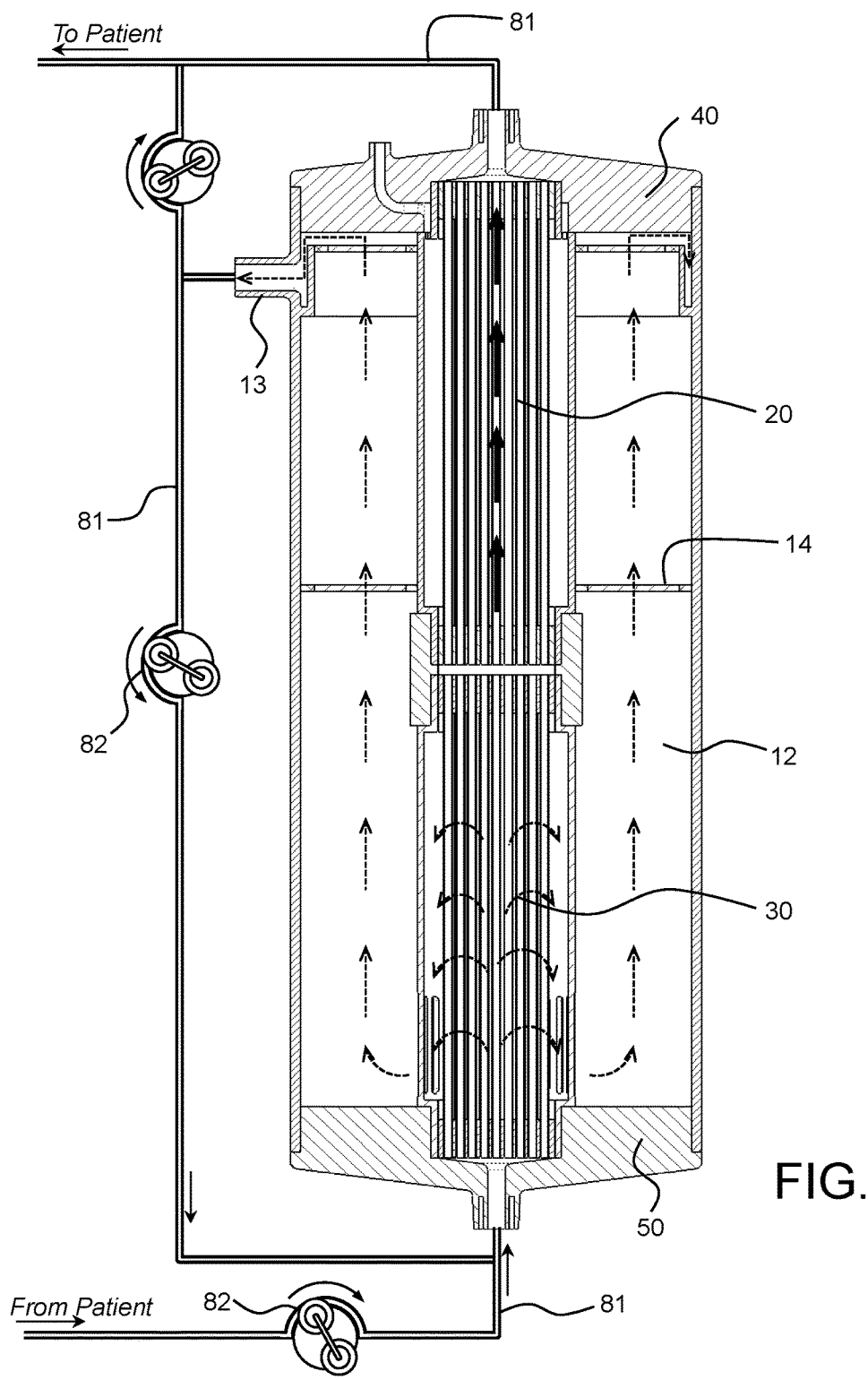
FIG. 7 is a view illustrating an exemplary flow inside a multi-functional filter.

As shown in FIG. 7, when blood flows into the multi-functional filter, by the pump 82, through the second cap 50, plasma is separated from blood in the second filter 30. The plasma separated across the second filter membrane 32 flows into the adsorption section 12 through the third flow hole 33 provided in the second filter container, and toxins and waste products are removed from the plasma due to the contact with adsorbent. The plasma passing the adsorption section returns, through the housing port 13, to the tube 81 in which blood flows.

Remaining blood of the second filter flows into the first filter 20 through the flow partitioning connector 60 and hemodialysis takes place therein. In order to purify blood passing through a side of the first filter membrane or the inside of the hollow-fiber membrane in case that the first filter membrane includes the hollow-fiber membrane, the dialysate needs to be supplied through the other side of the membrane, or through the outside of the hollow-fiber membrane. In this case, the dialysate may be supplied to the first filter and then discharged therefrom through the first flow path 71 which connects the first flow hole and the first flow passage. Dialysate may be used in a form of a dialysate bag or manufactured by adjusting, e.g., pH and electrolyte concentration in the ultrapure water prepared through a water treatment system.

Blood is not limited to flow into the second cap, and may be configured to flow into the first cap such that hemodialysis occurs in the first filter and then plasma is separated in the second filter. Accordingly, blood of a patient can be efficiently purified by hemodialysis in the first filter, plasma separation in the second filter, and the adsorption at the adsorption section.

Figure 6B:
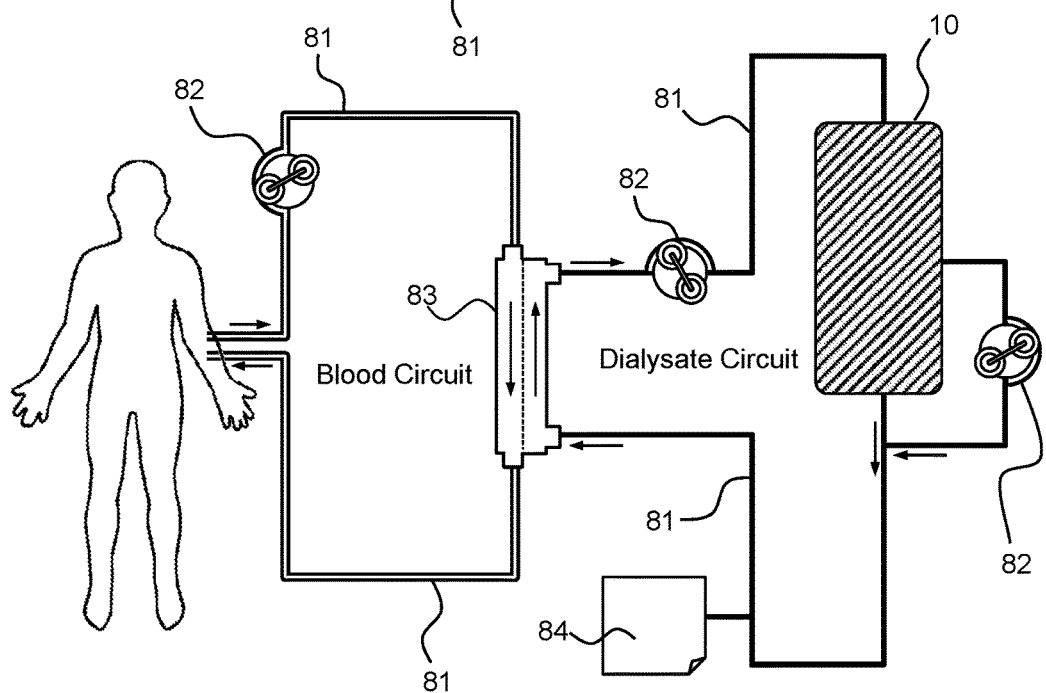

On the other hand, when the multi-functional filter does not make direct contact with blood of a patient, the blood purifying apparatus 80 according to an embodiment of the present invention may include a blood filter 83 in which mass transfer occurs between blood and dialysate, a blood circuit and a dialysate circuit with the blood filter 83 therebetween, as shown in FIG. 6B. The blood circuit includes a tube 81 connecting the blood filter and a patient and a pump 82 disposed on the tube 81 to transfer blood. Likewise, the dialysate circuit which removes toxins from blood may include a tube 81 where dialysate flows, a pump 82 to transfer dialysate, and the multi-functional filter 10 to purify used dialysate.

Figure 8:
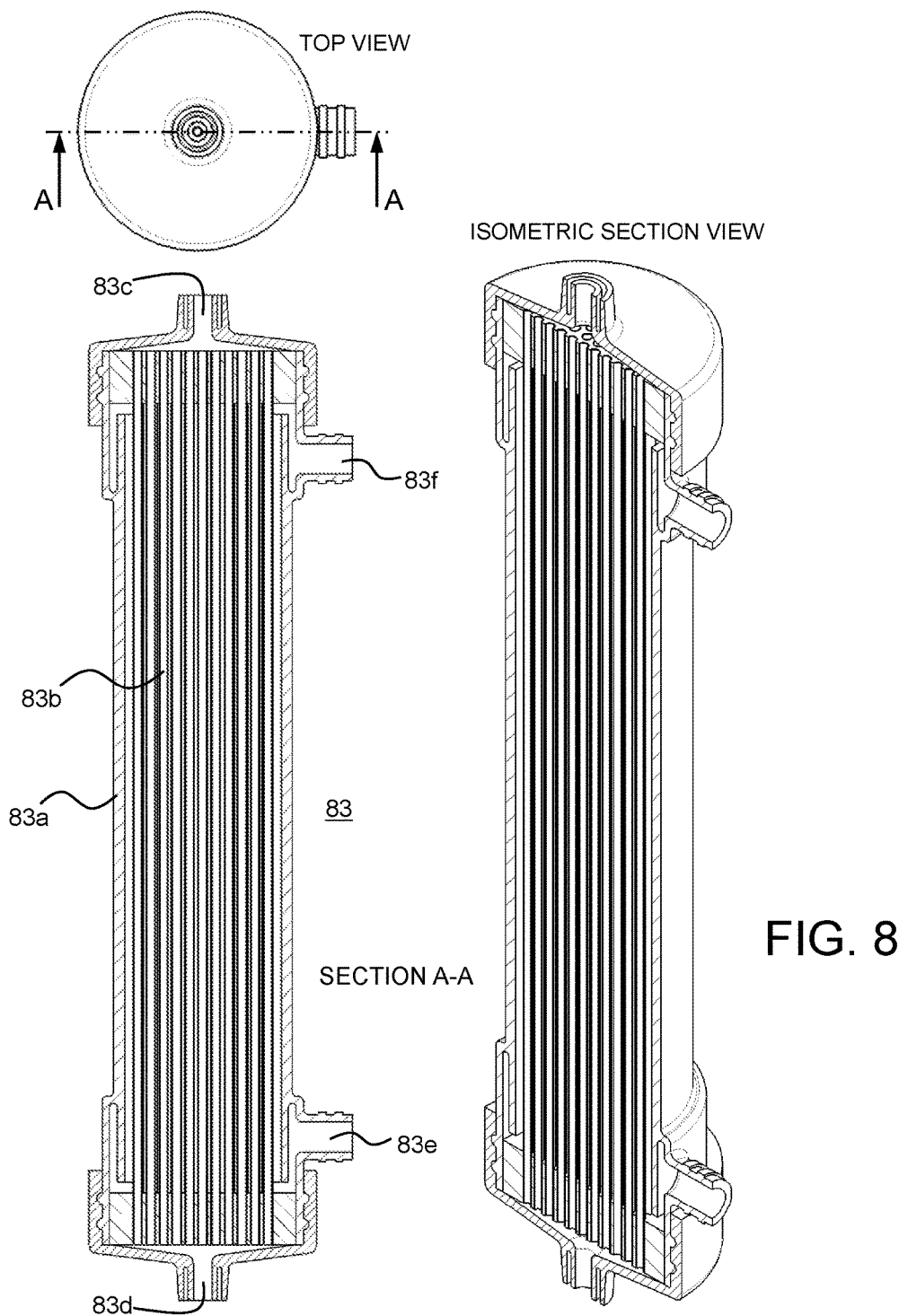
FIG. 8 is a cross-sectional view and a perspective view of a blood filter.

FIG. 8 illustrates an exemplary blood filter 83. The exemplar blood filter comprises a container 83a having an internal space and a blood filter membrane 83b accommodated in the internal space of the blood filter container. The internal space of the blood filter container may be divided into a blood flow region and a dialysate flow region by the blood filter membrane. The blood filter container includes a blood inlet 83c disposed at one end thereof and a blood outlet 84d disposed at the other end thereof. Also, a dialysate inlet 83e and a dialysate outlet 83f may be provided on the outer circumferential surface of the blood filter container.

The multi-functional filter 10 purifies used dialysate. As described above, dialysate may be manufactured by adjusting, e.g., pH and concentration of various electrolytes such as bicarbonate and sodium in the ultrapure water prepared through a water treatment system. Particularly, a plasma protein such as albumin may be added to the dialysate for liver dialysis because the albumin functions as a medium to remove protein-bound toxins existing in the blood or plasma. The multi-functional filter 10 rids used dialysate of toxins and waste products and adjusts concentration of electrolytes, thereby allowing the dialysate to be reused. The regenerated dialysate may be stored in a dialysate reservoir 84 and then supplied to the blood filter.

Figures 9A, 9B:
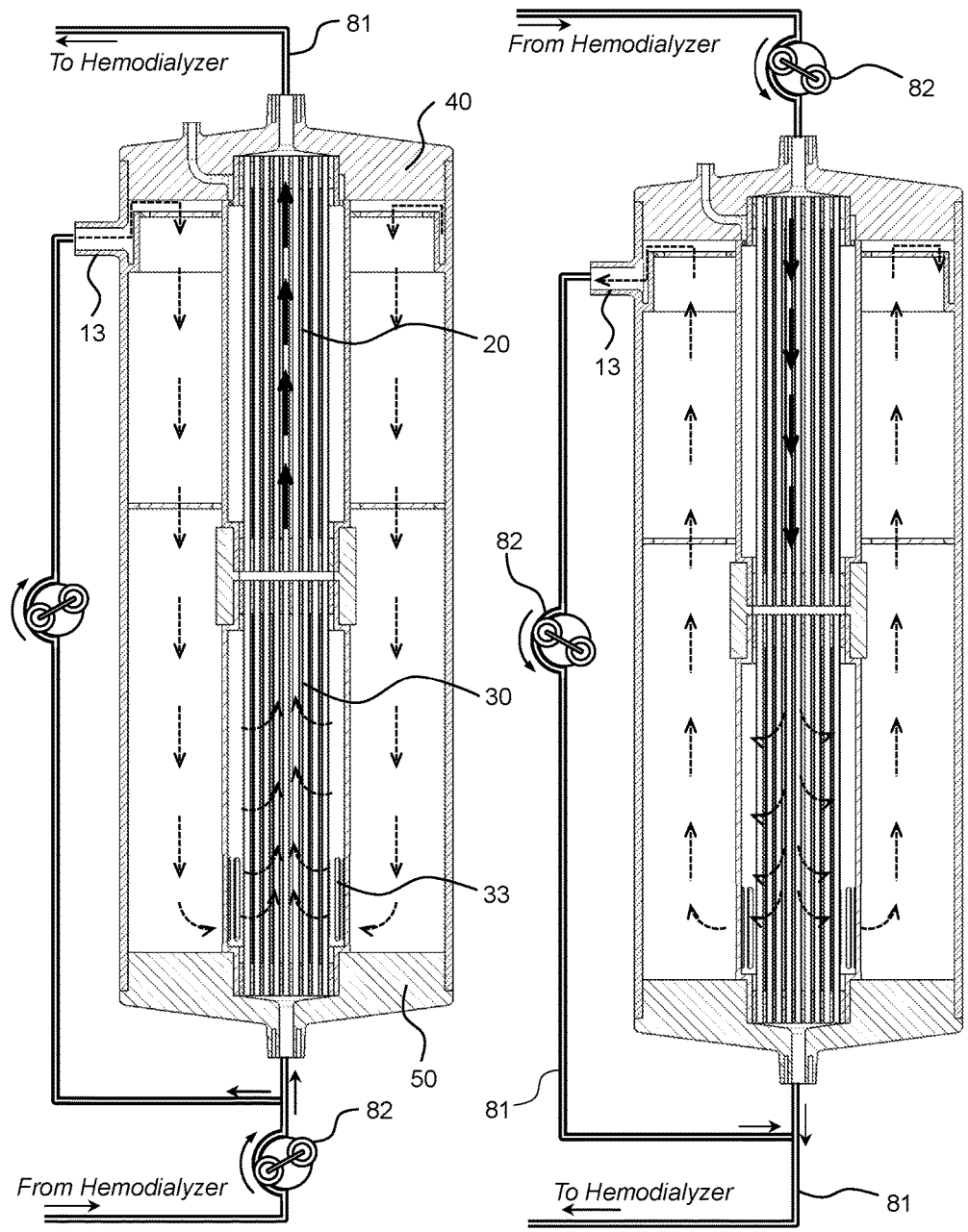
FIGS. 9A and 9B are views illustrating an exemplary flow inside a multi-functional filter.

FIGS. 9A and 9B illustrate an exemplary flow inside the multi-functional filter regenerating used dialysate. As shown in FIG. 9A, the used dialysate flows into the second filter 30 through the second cap port 51 by the pump 82. A portion of dialysate is separated and the separated dialysate flows into the adsorption section 12 where toxins in the dialysate are removed by the contact with adsorbents. The dialysate having passed the adsorption section 12 flows into the second filter through the third flow hole 33 provided in the second filter container 31, and then merged with dialysate flowing inside the second filter membrane across the second filter membrane.

Here, the amount of dialysate separated from the dialysate flowing into the multi-functional filter 10 and then supplied to the adsorption section is not limited to have a predetermined value, and may be determined in consideration of the amount of toxin that needs to be removed form the dialysate by the adsorption, the stability of dialysate flow passing thorough the multi-functional filter, etc. Thus, all of the used dialysate may flow into the adsorption section or all of the dialysate may be configured to pass through the second cap.

The dialysate having passed the second filter flows into the first filter 20 through the flow partitioning connector 60 and is purified again by the hemodialysis. Fresh dialysate may be supplied or discharged through the first flow path 71.

According to an exemplary embodiment of the present invention, the used dialysate is not limited to flow into the multi-functional filter 10 through the second cap 50, and may be configured to flow into the multi-functional filter through the first cap 40. In this case, a portion of dialysate flowing to the first cap is separated and supplied to the adsorption section 12. The dialysate which is not separated flows into the first filter and hemodialysis occurs therein. The dialysate moves to the second filter 30 where the dialysate having passed the adsorption section 12 is returned and mixed with the dialysate having passed the first filter, such that the dialysate of the second filter is supplied to the blood filter 83.

Alternatively, as shown in FIG. 9B, according to an embodiment of the dialysate flow through the multi-functional filter 10, the dialysate may flow into the first filter through the first cap and hemodialysis occurs in the first filter. Then, a portion of the dialysate is ultrafiltered in the second filter across the second filter membrane. The ultrafiltered dialysate is introduced to the adsorption section 12 through the third flow hole 33, and toxins are removed from the dialysate by the adsorption in the adsorption section. The dialysate having passed the adsorption section returns to the tube 81 in which dialysate flows.

Similarly, the amount of dialysate ultrafiltered in the second filter is not limited to have a predetermined value, but may be desirably determined in consideration of adsorption efficiency and flow stability. As such, the multi-functional filter 10 according to an embodiment of the present invention may have various configurations of dialysate flow in consideration of the purification efficiency and the stability in the flow of dialysate.

Various methods may be used for the pump 82 to transfer blood, plasma or dialysate. A roller pump having a roller which squeezes the tube 81 to transfer fluid therein and a roller driver rotating the roller is illustrated in FIGS. 6A, 6B and 7, but the pump 82 is not limited to the roller pump, and may be modified into other types of pumps that can transfer fluid. Exemplar pumps may include a centrifugal pump using centrifugal force to transfer fluid, a tube pressurizing pump including a tube pressurizing member compressing the tube and a tube pressurizing member driver, a piston pump comprising a cylinder and a piston that can compress or expand the cylinder, or a pneumatic pump that can compress or expand a fluid sac using a pneumatic driver.

Accordingly, the multi-functional filter 10 according to an embodiment of the present invention can efficiently purify blood or used dialysate through hemodialysis in the first filter, plasma separation or ultrafiltration in the second filter, and adsorption in the adsorption section.

Figures 10A, 10B:
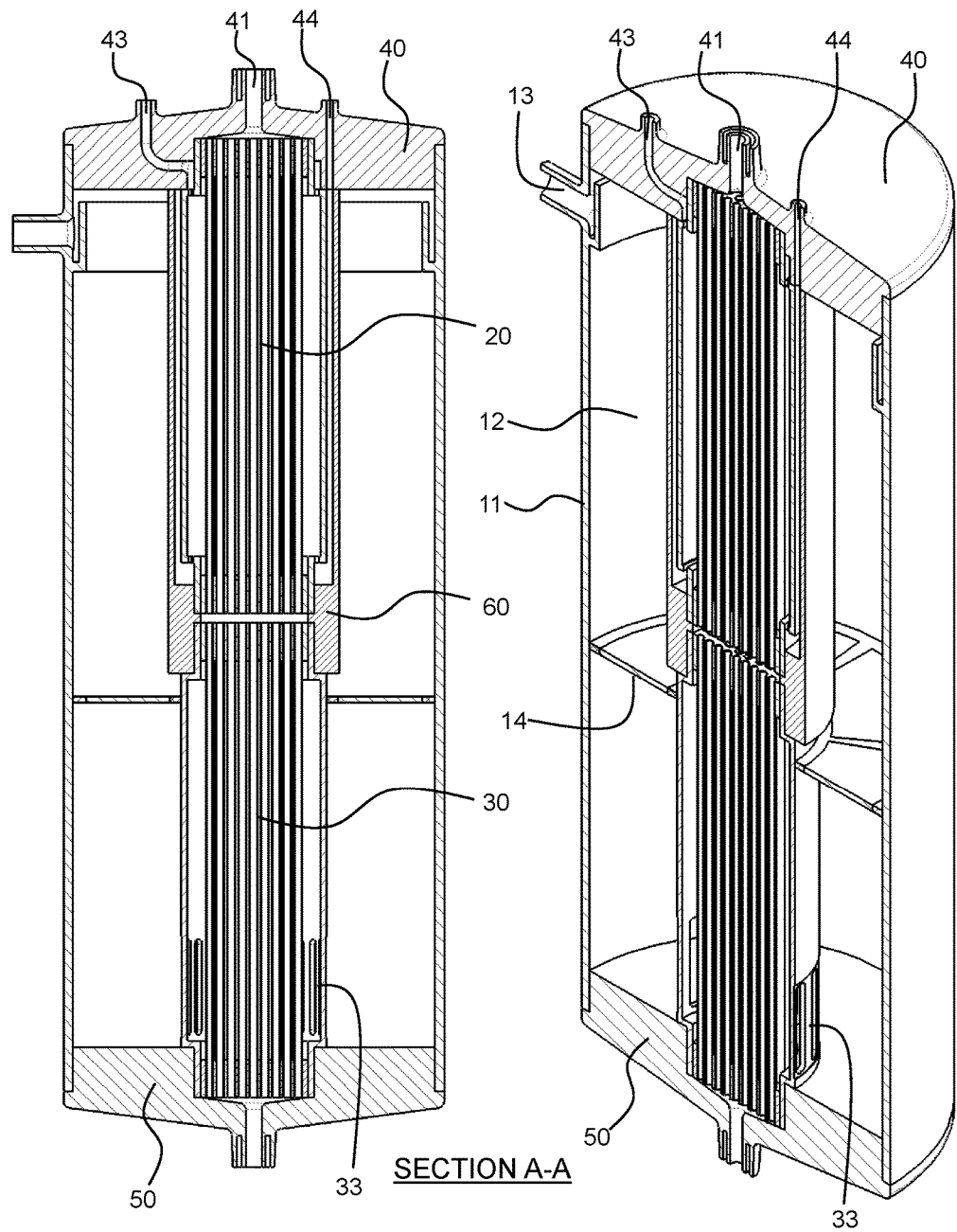
FIGS. 10A and 10B are a cross-sectional view and a perspective view of a multi-functional filter where inflow and outflow of dialysate through a first filter are separated from each other.

Here, the multi-functional filter 10 may be modified into a structure in which a flow path to supply dialysate to the first filter 20 and a flow path to discharge dialysate therefrom are separated from each other. When blood or used dialysate flow into a side of the first filter membrane 22, fresh dialysate may flow through the other side thereof to perform hemodialysis. In this case, the hemodialysis efficiency may be further improved by separating the inflow and the outflow of dialysate. FIGS. 10A and 10B illustrate the multi-functional filter having a second flow path, as well as the first flow path 71, to separate the inflow and outflow of dialysate through the first filter. The cutting section A-A in FIGS. 10A and 10B represent a cutting section of the top view of the multi-functional filter, as shown in FIG. 1.

Figures 11A, 11B:
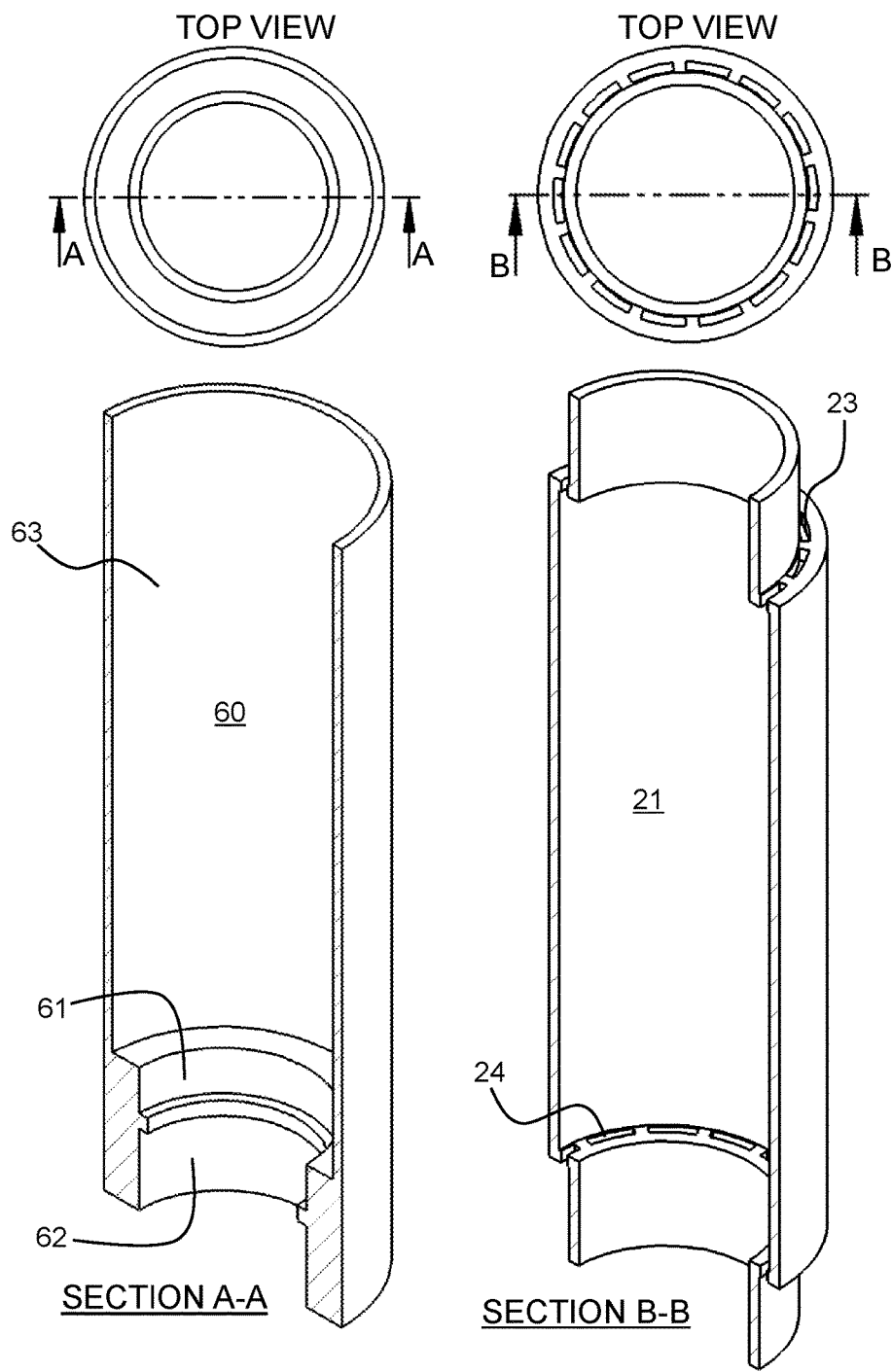
FIGS. 11A and 11B are views illustrating a flow partitioning connector and a container of a first filter, respectively.

To this end, as shown in FIG. 11A, the flow partitioning connector 60 may further include a first filter accommodation space 63, as well as the connecting portions 61 and 62, which accommodates the first filter 20 to define a dialysate flow path outside the first filter. An end of the first filter accommodation space 63 may be coupled to the first cap. Also, as shown in FIG. 11B, the first filter container 21 may further be provided with a second flow hole 24 surrounding the container 21 along a circumferential direction. The second flow hole 24 may be desirably provided in an opposite side to the position where the first flow hole 23 is provided with respect to a longitudinal middle portion of the container.

In addition, as shown in FIG. 10B, the first cap 40 may additionally include a second flow passage 44 connecting a surface of the cap facing to the adsorption section and the outer surface of the cap, as well as the first flow passage 43 connecting the first cap connecting portion 42 and the outer surface of the cap. The second flow passage 44 may penetrate the cap.

The second flow path 72 may be formed by the coupling of the flow partitioning connector 60, the first filter 20, and the first cap 40. As shown in FIGS. 12A and 12B, the first filter 20 is seated in the first filter accommodation space 63 of the flow partitioning connector 60 and an end of the first filter is coupled to the connecting portion 61 of the flow partitioning connector, thereby allowing dialysate of the first filter to flow into the first filter accommodation space 63 through the second flow hole 24. In addition, as shown in FIG. 12C, the flow partitioning connector 60 and the first cap 40 are coupled to each other, allowing dialysate of the first filter accommodation space 63 to flow through the second flow passage 44 of the first cap 40. Thus, the coupling of the first filter, the flow partitioning connector, and the first cap forms the second flow path 72 in which the first filter, the second flow hole, first filter accommodation space, and the second flow passage are connected.

As such, dialysate is limited to flow into a predetermined space due to the coupling of the first cap 40, the first filter 20, and the flow partitioning connector 60, and as described above, various methods can be used to limit the flow into the predetermined space.

Figure 13A:
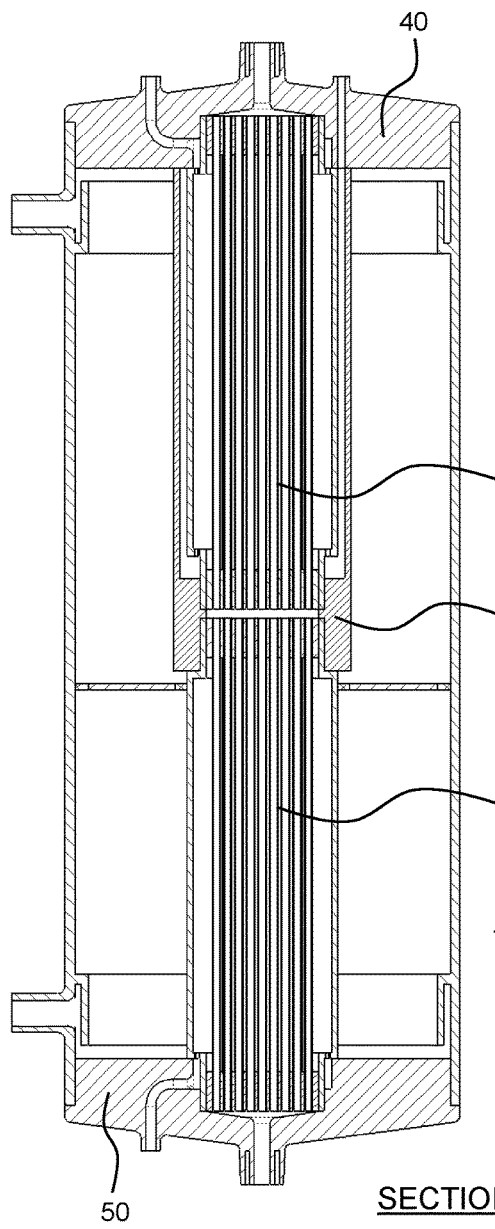
FIGS. 13A and 13B are a cross-sectional view and a perspective view illustrating a multi-functional filter where a third flow passage is configured to pass through a second cap.
Figure 13B:
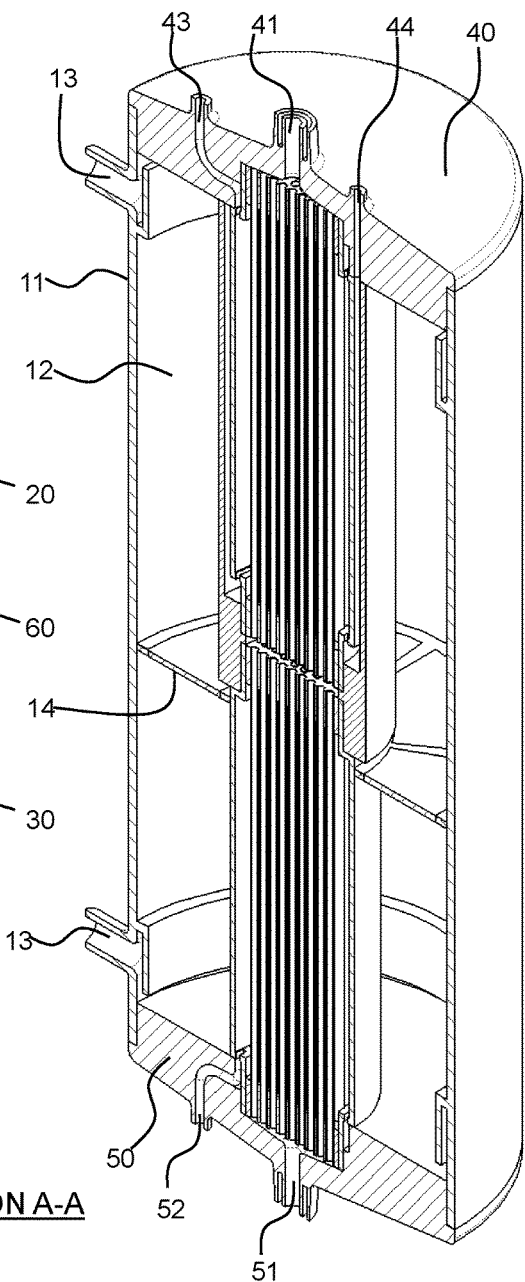

According to an exemplary flow inside the multi-functional filter 10 illustrated in FIGS. 7, 9A and 9B, plasma separated or dialysate ultrafiltered in the second filter 30 flows into the adsorption section through the third flow hole 33. In other words, the second filter and the adsorption section are connected to each other through the third flow hole. However, the multi-functional filter 10 according to an embodiment of the present invention is not limited to the structure shown in the drawings, and may be modified into a structure where fluid of the second filter 30 is discharged out of the second filter through the second cap and then supplied to the adsorption section, as shown in FIGS. 13A and 13B. In a similar manner, the cutting section A-A in FIGS. 13A and 13B represents a cutting section of the top view of the multi-functional filter.

Figure 14:
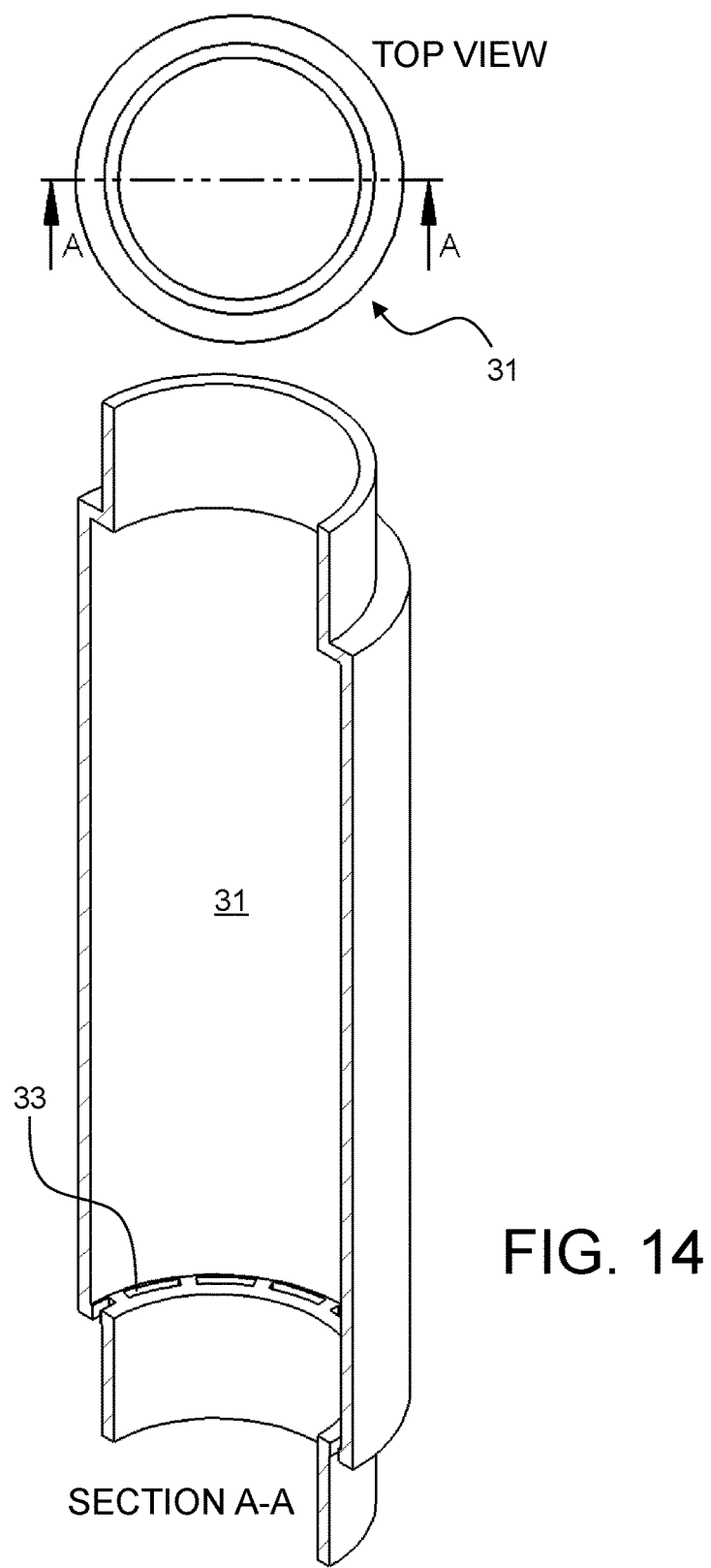
FIG. 14 is a view illustrating a container of a second filter including a third flow hole.

To this end, the third flow hole 33 may be provided in the second filter container at a place which is connected to the second cap 50 as shown in FIG. 14. The second cap 50 may be provided with a third flow passage 53, opposite ends of which are connected to the second cap connecting portion 52 and the outer surface of the second cap 50. FIG. 13B illustrates the second cap including the third flow passage.

As described above, the second filter 30 and the second cap 50 are coupled to each other by seating an end of the second filter container 31 in the second cap connecting portion 52. When the second filter and the second cap are coupled to each other, the fluid passing through the third flow hole 33 is limited to flow into the third flow passage 53 provided in the second cap 50. The third flow path 73 created due to the coupling of the second filter and the second cap can be formed under the same principle as that of forming the first flow path shown in FIG. 4. That is, the coupling of the second filter and the second cap forms the third flow path 73 that connects the second filter 30, the third flow hole 33, and the third flow passage 53. The fluid in the second filter 30 can be discharged out of the second filter and then supplied to the adsorption section.

Figure 15:
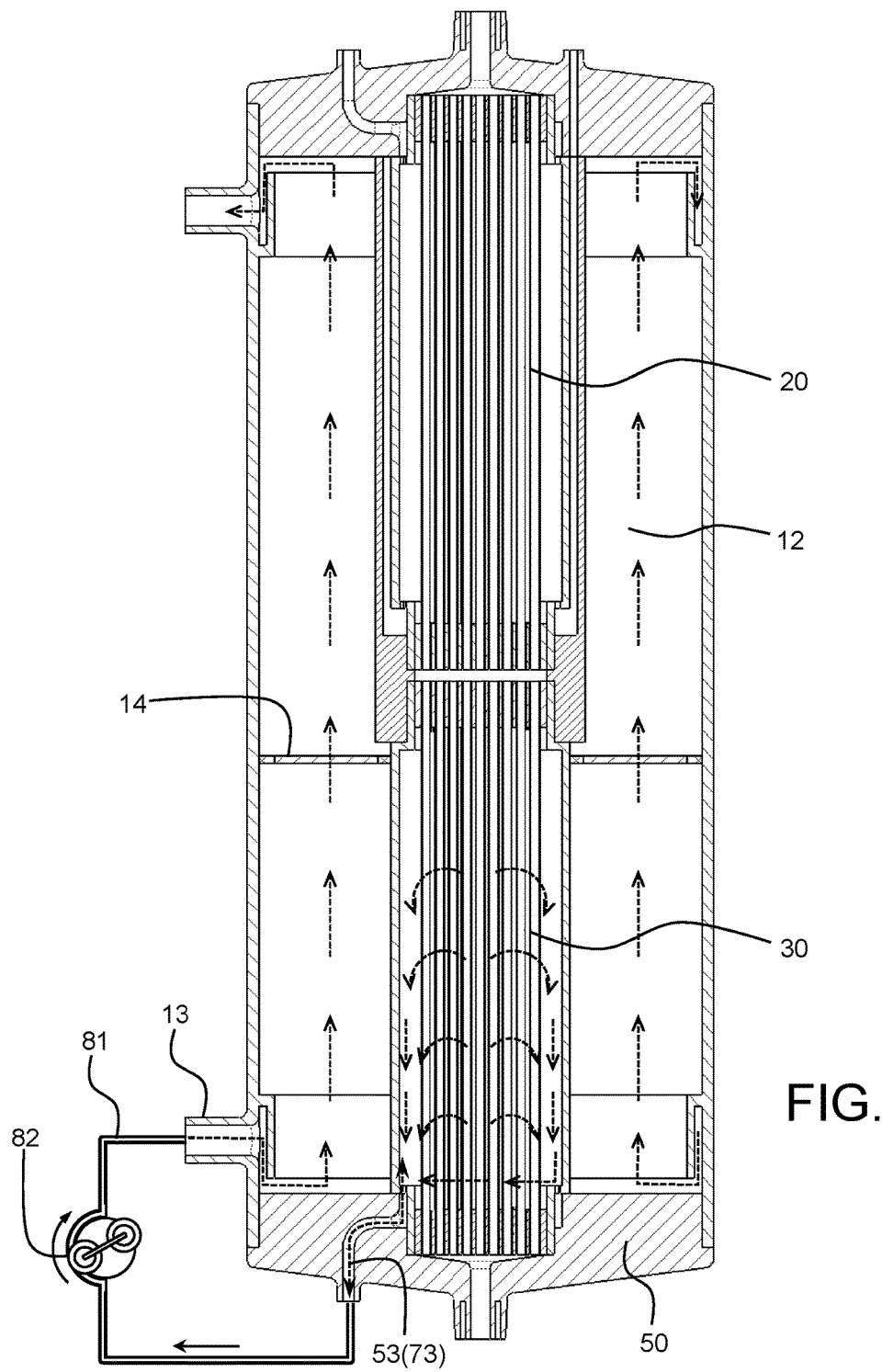
FIG. 15 is a view illustrating an exemplary flow inside a multi-functional filter where a third flow passage is configured to pass through a second cap.

FIG. 15 illustrates an exemplary flow inside the multi-functional filter having the third flow path. Plasma separated or dialysate ultrafiltered in the second filter 30 is discharged out of the second filter through the third flow path 73 and supplied to the adsorption section through the tube 81 connecting the third flow passage 53 and the housing port 13. In this case, a pump 82 may be provided on the tube connecting the third flow passage 53 and the housing port 13 to facilitate the flow through the adsorption section.

Figure 16B:
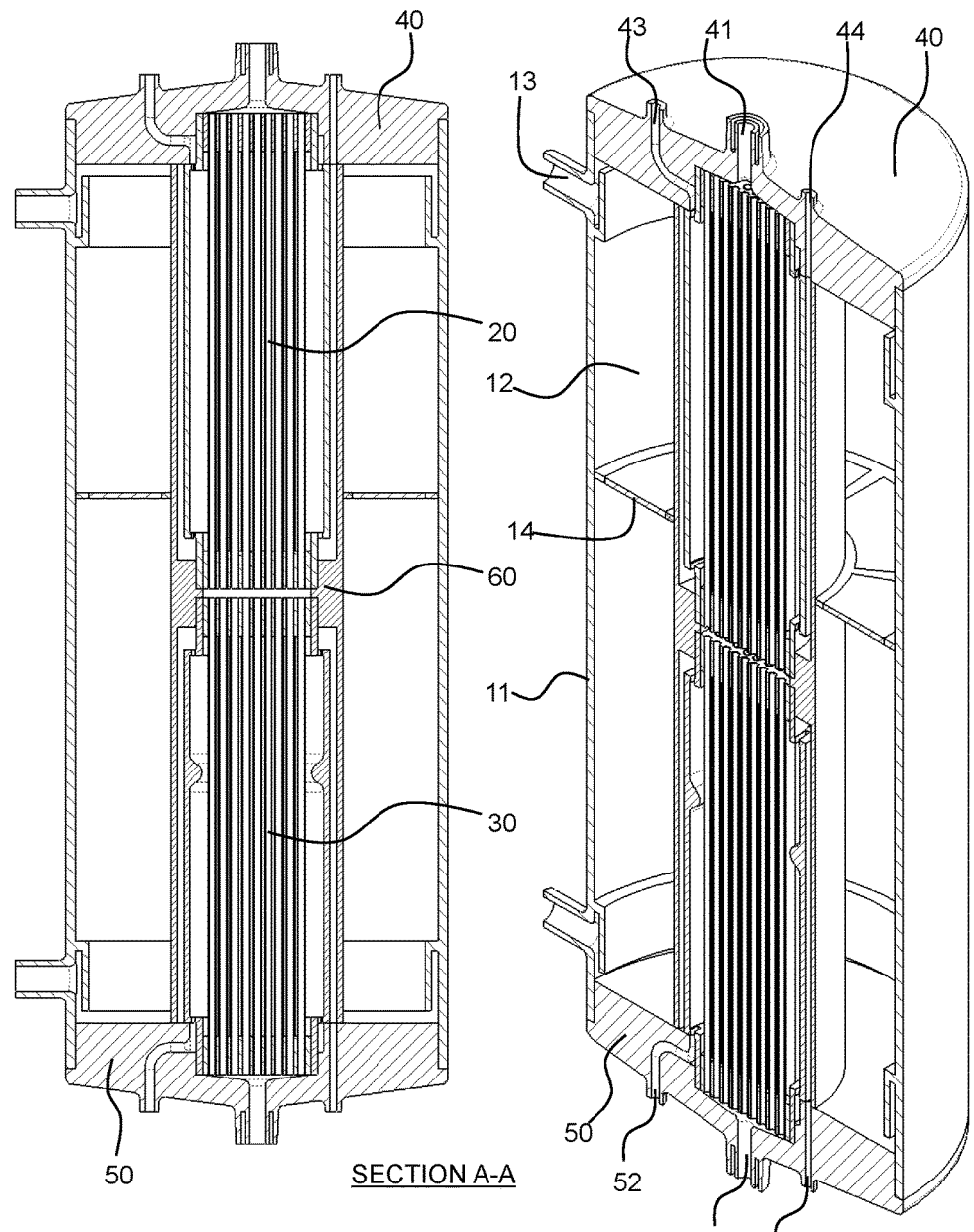

In a similar manner with the first and second flow paths 71 and 72 separating inflow and outflow of dialysate through the first filter 20, the multi-functional filter 10 according to an embodiment of the present invention may be modified to include a fourth flow path, as well as the third flow path 73, so as to separate inflow and outflow of a fluid through the second filter. FIGS. 16A and 16B illustrate the multi-functional filter having the fourth flow path outside the second filter 30. The cutting section A-A in the drawings represents a cutting section of the top view of the multi-functional filter.

Figures 17A, 17B:
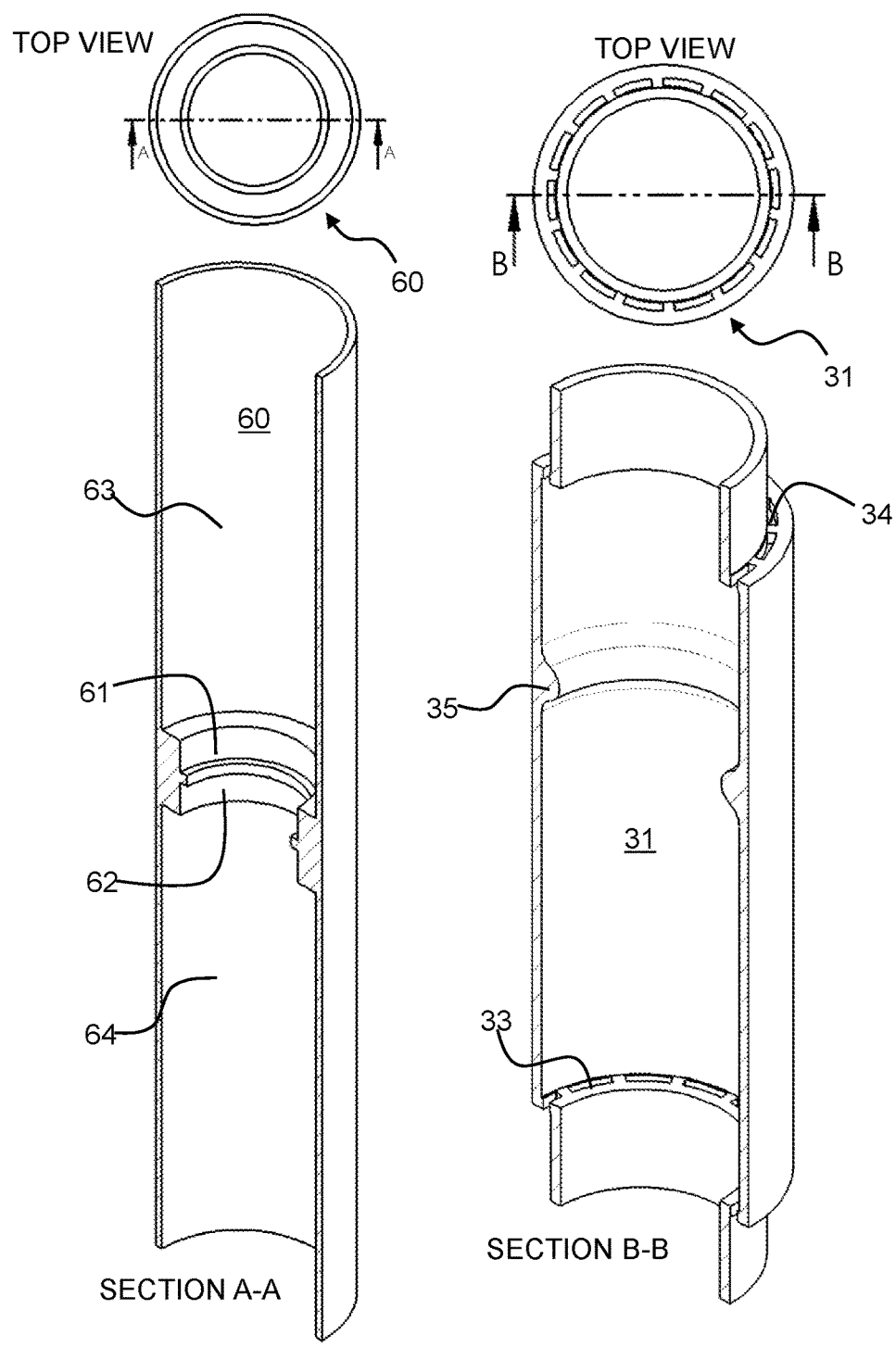
FIGS. 17A and 17B are views illustrating a flow partitioning connector and a container of a second filter including a fourth flow hole, respectively.

In order to form the fourth flow path, as shown in FIG. 17A, the flow partitioning connector 60 may further include a second filter accommodation space 64 that accommodates the second filter 30 and defines a flow path outside the second filter. One end of the second filter accommodation space 64 may be coupled to the second cap.

Also, as shown in FIG. 17B, the second filter container 31 may further be provided with a fourth flow hole 34 surrounding the container 31 along a circumferential direction, as well as the third flow hole 33 disposed in the container at a place to which the second cap 50 is connected. The fourth flow hole 34 may be desirably disposed in an opposite side to the place where the third flow hole 33 is provided with respect to a longitudinal middle portion of the container.

Also, the second cap 50 may additionally include the fourth flow passage 54 connecting a surface of the cap facing to the adsorption section and the outer surface thereof. FIG. 16B illustrates the second cap 50 having the fourth flow passage.

FIGS. 18A, 18B and 18C illustrate the fourth flow path 74 formed through the coupling of the flow partitioning connector 60, the second filter 30, and the second cap 50. As shown in FIGS. 18A and 18B, the second filter 30 is seated in the second filter accommodation space 64 of the flow partitioning connector 60 and an end of the second filter is coupled to the connecting portion 62 of the flow partitioning connector, thereby allowing the fluid of the second filter to flow into the second filter accommodation space 64 through the fourth flow hole 34. Also, as shown in FIG. 18C, the flow partitioning connector 60 and the second cap 50 are coupled to each other, allowing the fluid of the second filter accommodation space 64 to flow through the fourth flow passage 54 of the second cap 50. Thus, the fourth flow path 74 can be formed, in which the second filter, the fourth flow hole, the second filter accommodation space, and the fourth flow passage forms are connected. When a fluid of the second filter is discharged through one of the third flow path 73 and the fourth flow path 74, the fluid may be desirably supplied to the second filter through the other one.

Figure 19:
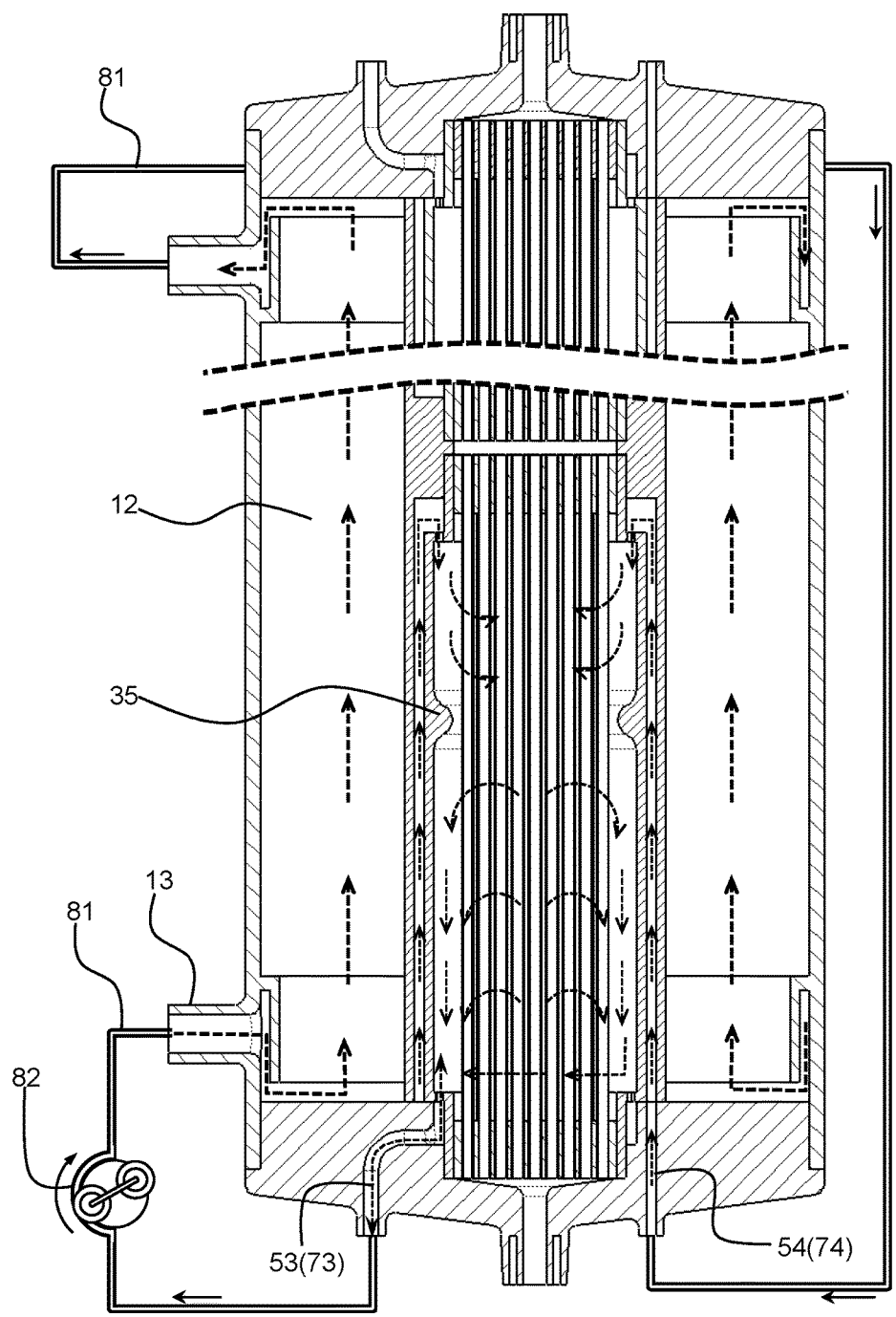
FIG. 19 is a view illustrating an exemplary flow inside a multi-functional filter having a fourth flow passage.

FIG. 19 illustrates an exemplary flow inside the multi-functional filter 10 having the fourth flow path 74. The fluid separated across the second filter membrane is discharged through the third flow path 73 and then supplied to the adsorption section through the tube 81 connecting the second cap 50 and the housing port 13. The fluid passes through the adsorption section, removing toxins and waste products therein, and then returns to the second filter through the fourth flow path 74. In this case, a pump 82 may be disposed on the tube connecting the second cap and the housing port to facilitate the flow through the adsorption section.

In the exemplary flow shown in FIG. 19, the plasma or dialysate may be separated across the second filter membrane 32 at a place close to the second cap 50, and the separated fluid passing through the adsorption section 12 returns to the second filter membrane 32 at an opposite side to the second cap 50. When the fluid separation and the fluid return occur within the second filter, it may be possible that the fluid returning to the second filter through the fourth flow path 74 is discharged out of the second filter through the third flow path 73 without flowing into the inside of the second filter membrane. Accordingly, in order to prevent such recirculation of fluid, as shown in FIG. 19 or FIG. 17B, a wall protruder 35 may be provided in an inner surface of the second filter container. The wall protruder 35 reduces an inner diameter of the second filter container 31, having a role of dividing the internal space of the second filter into a region through which the separated fluid is discharged and a region through which the separated fluid is returned.

The wall protruder may also be disposed in the first filter container 21, such that a greater change in the pressure of dialysate can be achieved when dialysate passes through the first filter, thereby improving hemodialysis efficiency by filtration.

Figure 20B:
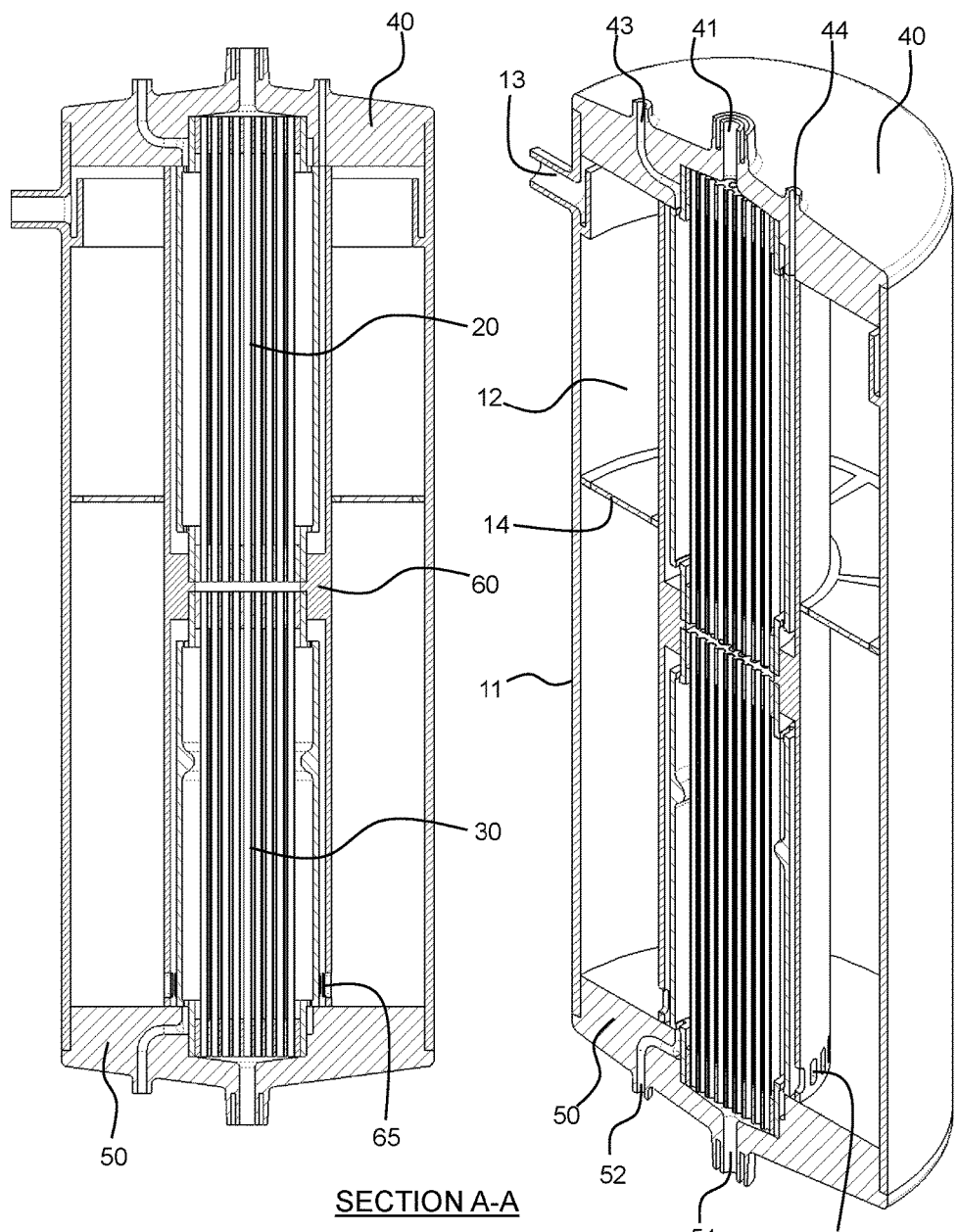

Finally, the fourth flow path 74 is not limited to pass through the second cap. As shown in FIGS. 20A and 20B, a fluid passing through the adsorption section 12 may be returned directly to the second filter 30 through a flow partitioning connector hole 65 provided in the flow partitioning connector 60 at a side close to the second cap without passing through the housing port 13. Thus, the housing port 13 and the flow partitioning connector hole 65 may be desirably provided at the opposite side of each other along a longitudinal direction of the multi-functional filter, such that a fluid having passed the housing port 13 can sufficiently contact the adsorbent inside the adsorption section and then be discharged to the second filter. In this case, the fourth flow passage 54 provided in the second cap may be unnecessary.

Figure 21:
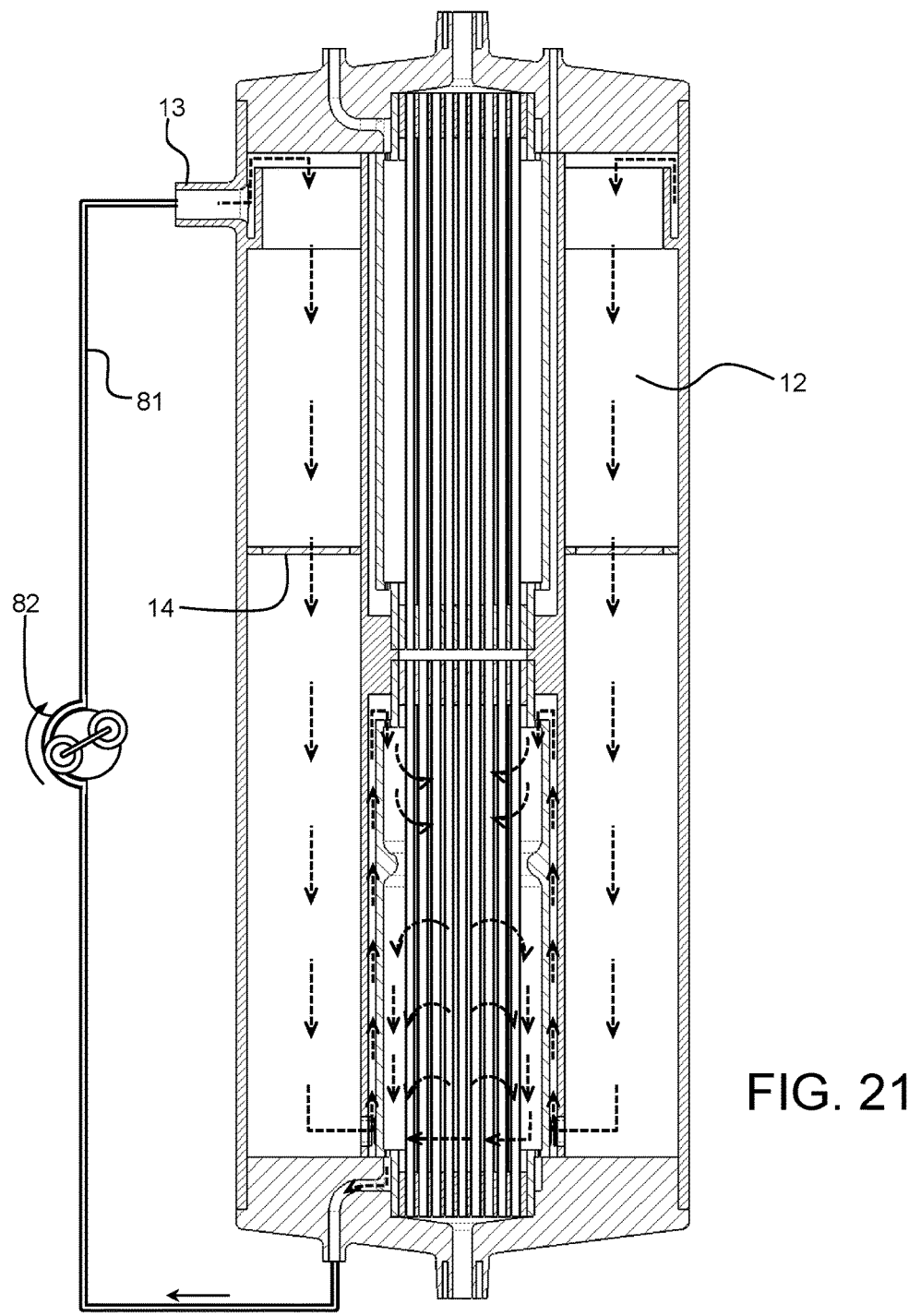
FIG. 21 is a view illustrating an exemplary flow inside a multi-functional filter.

FIG. 21 illustrates an exemplary flow inside the multi-functional filter including the flow partitioning connector hole 65. A fluid separated in the second filter 30 is discharged through the third flow path 73 and then supplied to the adsorption section through a tube 81 connecting the third flow passage and the housing port. The fluid passes through the adsorption section in which toxins and waste products are removed and then returns to the second filter passing through the flow partitioning connector hole 65, the second filter accommodation space 64, and the fourth flow hole 34.

Here, aforementioned various methods can be used to prevent the adsorbent from passing through the housing port 13 or the flow partitioning connector hole 65.

Accordingly, exemplary embodiments of the present invention provide the multi-functional filter 10 in which dialysis, adsorption, and ultrafiltration or plasma separation are integrated to purify blood or used dialysate and the blood purifying apparatus which is configured to simplify the whole apparatus by facilitating the flow inside the filter, provide convenience in installation and use, and reduce the treatment cost.

The embodiment of the present invention described above and illustrated in the drawings should not be construed as limiting the technical spirit of the present invention. The scope of the present invention should be defined as disclosed in the accompanying claims, and those skilled in the art will appreciate that various modifications, additions and substitutions are possible without departing from the scope and spirit of the invention.

What is claimed is:

1. A multi-functional filter, comprising:
a first filter including a container having an internal space and a separation membrane accommodated in the internal space of the container;
a second filter including a container having an internal space and a separation membrane accommodated in the internal space of the container;
a housing providing an installation space for the first filter and the second filter and defining an adsorption section outside the first filter and the second filter;
a housing port provided in the housing to allow a fluid to flow through the adsorption section; and
a flow partitioning connector connecting the first filter and the second filter to prevent a leakage of a fluid between the first filter and the second filter, wherein the first filter container and the second filter container each comprise a flow hole in at least one side along a longitudinal direction with respect to a longitudinal middle portion thereof, and wherein the housing comprises a wall, a first cap coupled to the first filter at one side of the wall, and a second cap coupled to the second filter at the other side of the wall.

2. The multi-functional filter of claim 1, wherein at least one of the first cap and the second cap comprises a flow passage that penetrates the cap, an end of the flow passage adjacent to a connecting portion of the cap.

3. The multi-functional filter of claim 2, wherein the flow partitioning connector is connected to at least one of the first cap and the second cap, and the cap connected to the flow partitioning connector further comprises a second flow passage that penetrates the cap, an end of the second flow passage adjacent to a surface of the cap facing to the adsorption section.

4. The multi-functional filter of claim 3, comprising an adsorbent in the adsorption section to remove toxins and waste product.

5. The multi-functional filter of claim 4, wherein in order to prevent the adsorbent from moving through the housing port or the flow hole, the housing port or the flow hole is formed to have a size smaller than the adsorbent, the housing port or the flow hole is covered by a mesh filter with pores having a smaller size than the adsorbent, the adsorbent is covered by a mesh filter with pores having a smaller size than the adsorbent, an adsorbent block in which powder or particles are compressed is used, or a separation wall is disposed to inhibit passing of the adsorbent.

6. The multi-functional filter of claim 5, wherein the separation wall has pores of a smaller size than the adsorbent or has a structure in which a mesh filter having pores of a smaller size than the adsorbent is attached to a support wall through which a fluid flows.

7. A blood purifying apparatus, comprising:
a multi-functional filter according to claim 5;
a tube connected to the multi-functional filter to allow blood or plasma to flow therethrough; and
a pump disposed on the tube to transfer blood or plasma.

8. The blood purifying apparatus of claim 7, wherein one of the first filter membrane and the second filter membrane comprises a dialysis membrane and the other one of the first filter membrane and the second filter membrane comprises a plasma separation membrane.

9. A blood purifying apparatus, comprising:
a blood filter where blood and dialysate pass and mass transfer occurs therebetween;
a tube in which blood or dialysate flows, the tube connected to the blood filter; and
a multi-functional filter according to claim 5 to purify dialysate.

10. The multi-functional filter of claim 4, wherein the first filter container or the second filter container comprises a wall protruder disposed in an inner wall of the container to reduce an internal diameter thereof.

11. The multi-functional filter of claim 2, wherein opposite ends of the flow partitioning connector are connected to the first cap and the second cap, and one of the first cap and the second cap comprises a second flow passage that penetrates the cap, an end of the second flow passage adjacent to a surface of the cap facing to the adsorption section, and wherein the flow partitioning connector includes a flow hole surrounding the flow partitioning connector along a circumferential direction and allowing a fluid to flow therethrough.

12. The multi-functional filter of claim 11, comprising an adsorbent in the adsorption section to remove toxins and waste product.

13. The multi-functional filter of claim 12, wherein in order to prevent the adsorbent from moving through the housing port or the flow hole, the housing port or the flow hole is formed to have a size smaller than the adsorbent, the housing port or the flow hole is covered by a mesh filter with pores having a smaller size than the adsorbent, the adsorbent is covered by a mesh filter with pores having a smaller size than the adsorbent, an adsorbent block in which powder or particles are compressed is used, or a separation wall is disposed to inhibit passing of the adsorbent.

14. The multi-functional filter of claim 13, wherein the separation wall has pores of a smaller size than the adsorbent or has a structure in which a mesh filter having pores of a smaller size than the adsorbent is attached to a support wall through which a fluid flows.

15. The multi-functional filter of claim 12, wherein the first filter container or the second filter container comprises a wall protruder disposed in an inner wall of the container to reduce an internal diameter thereof.

16. The multi-functional filter of claim 1, wherein the flow partitioning connector has a portion that contacts at least one of the first filter container and the second filter container.

* * * * *